United States Patent
Colgan et al.

(10) Patent No.: US 6,520,983 B1
(45) Date of Patent: Feb. 18, 2003

(54) STENT DELIVERY SYSTEM

(75) Inventors: Darragh Colgan, Galway (IE); Peter A. Hamilton, East Bridgewater, MA (US); Paul DiCarlo, Middleboro, MA (US); Andrew J. Campbell, Reading, MA (US); Sean Gilligan, Galway (IE); Albert Chin, Newton Highlands, MA (US); Kristian DiMatteo, Watertown, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/270,949

(22) Filed: Mar. 17, 1999

Related U.S. Application Data

(63) Continuation-in-part of application No. 09/052,214, filed on Mar. 31, 1998.

(51) Int. Cl.$^7$ .................................................. A61F 2/06

(52) U.S. Cl. ..................................... 623/1.11; 623/1.12

(58) Field of Search ............................. 623/1.11, 1.12, 623/1.13, 1.14, 1.15, 1.16, 1.17, 1.18, 1.2, 1.23; 606/108, 191, 194, 19 R

(56) References Cited

U.S. PATENT DOCUMENTS

| | | | |
|---|---|---|---|
| 3,868,956 A | 3/1975 | Alfidi et al. ................ 128/345 |
| 4,776,337 A | 10/1988 | Palmaz ....................... 128/343 |
| 4,922,905 A | 5/1990 | Strecker ...................... 606/195 |
| 4,990,151 A | 2/1991 | Wallstén ...................... 606/108 |
| 4,994,071 A | 2/1991 | MacGregor ................. 606/194 |
| 5,015,253 A | 5/1991 | MacGregor ..................... 623/1 |
| 5,019,090 A | 5/1991 | Pinchuk ....................... 606/194 |
| 5,026,377 A | 6/1991 | Burton et al. ............... 606/108 |
| 5,061,275 A | 10/1991 | Wallstén et al. ................ 623/1 |
| 5,064,435 A | 11/1991 | Porter ............................ 623/12 |
| 5,133,732 A | 7/1992 | Wiktor ........................ 606/195 |
| 5,159,920 A | 11/1992 | Condon et al. ................. 128/6 |
| 5,171,262 A | 12/1992 | MacGregor ..................... 623/1 |
| 5,201,901 A | 4/1993 | Harada et al. ............... 606/198 |
| 5,211,658 A | 5/1993 | Clouse ........................... 623/1 |
| 5,256,158 A | 10/1993 | Tolkoff et al. ............... 604/280 |
| 5,282,823 A | 2/1994 | Schwartz et al. ............ 606/198 |
| 5,304,220 A | 4/1994 | Maginot ......................... 623/1 |
| 5,366,504 A | 11/1994 | Andersen et al. ............. 623/11 |
| 5,382,259 A | 1/1995 | Phelps et al. ................ 606/151 |
| 5,405,377 A | 4/1995 | Cragg ............................. 623/1 |
| 5,405,378 A | 4/1995 | Strecker ......................... 623/1 |
| 5,411,507 A | 5/1995 | Heckele ....................... 606/108 |
| 5,484,444 A | 1/1996 | Braunschweiler et al. ... 606/108 |
| 5,534,007 A | 7/1996 | St. Germain et al. ........ 606/108 |
| 5,534,287 A | 7/1996 | Lukic ......................... 427/2.25 |

(List continued on next page.)

FOREIGN PATENT DOCUMENTS

| | | |
|---|---|---|
| EP | 0 744 163 A1 | 11/1996 |
| EP | 0 788 012 A2 A3 | 6/1997 |
| EP | 0 788 802 A2 | 8/1997 |
| EP | 0 804 934 A2 | 11/1997 |
| EP | 0 812 579 A1 | 12/1997 |
| EP | 894 505 A2 | 2/1999 |
| EP | 0 941 716 716 A2 | 9/1999 |
| WO | 87/04935 | 8/1987 |
| WO | 94/00178 | 1/1994 |
| WO | 95/29646 | 11/1995 |
| WO | 96/32078 | 10/1996 |
| WO | 96/33677 | 10/1996 |
| WO | 96/41589 | 12/1996 |
| WO | 97/32546 | 9/1997 |

*Primary Examiner*—Henry J. Recla
*Assistant Examiner*—Vy Q. Bui
(74) *Attorney, Agent, or Firm*—Ratner & Prestia

(57) ABSTRACT

The present invention relates to a system for delivering a medical prosthesis into a body lumen. A preferred embodiment of the invention utilizes a catheter having a stent mounted at the distal end that is released into the body lumen by movement of an outer sheath covering the stent in the proximal direction. The stent expands to conform to the inner wall of the lumen and the catheter is withdrawn.

12 Claims, 39 Drawing Sheets

U.S. PATENT DOCUMENTS

| | | | |
|---|---|---|---|
| 5,571,167 A | 11/1996 | Maginot | 623/1 |
| 5,603,698 A | 2/1997 | Roberts et al. | 604/104 |
| 5,607,466 A | 3/1997 | Imbert et al. | 623/1 |
| 5,643,339 A | 7/1997 | Kavteladze et al. | 623/1 |
| 5,645,559 A | 7/1997 | Hachtman et al. | 606/198 |
| 5,653,727 A | 8/1997 | Wiktor | 606/195 |
| 5,702,373 A * | 12/1997 | Samson | 604/282 |
| 5,702,418 A | 12/1997 | Ravenscroft | 606/198 |
| 5,725,571 A | 3/1998 | Imbert et al. | 623/1 |
| 5,725,572 A | 3/1998 | Lam et al. | 623/1 |
| 5,728,150 A | 3/1998 | McDonald et al. | 623/1 |
| 5,728,158 A | 3/1998 | Lau et al. | 623/12 |
| 5,797,952 A * | 8/1998 | Klein | 606/198 |
| 5,800,519 A | 9/1998 | Sandock | 623/1 |
| 5,843,168 A | 12/1998 | Dang | 623/1 |
| 5,876,432 A | 3/1999 | Lau et al. | 623/1 |
| 5,928,280 A | 7/1999 | Hansen et al. | 623/1 |
| 5,968,052 A * | 10/1999 | Sullivan, III et al. | 606/108 |
| 6,019,778 A * | 2/2000 | Wilson et al. | 606/198 |

* cited by examiner

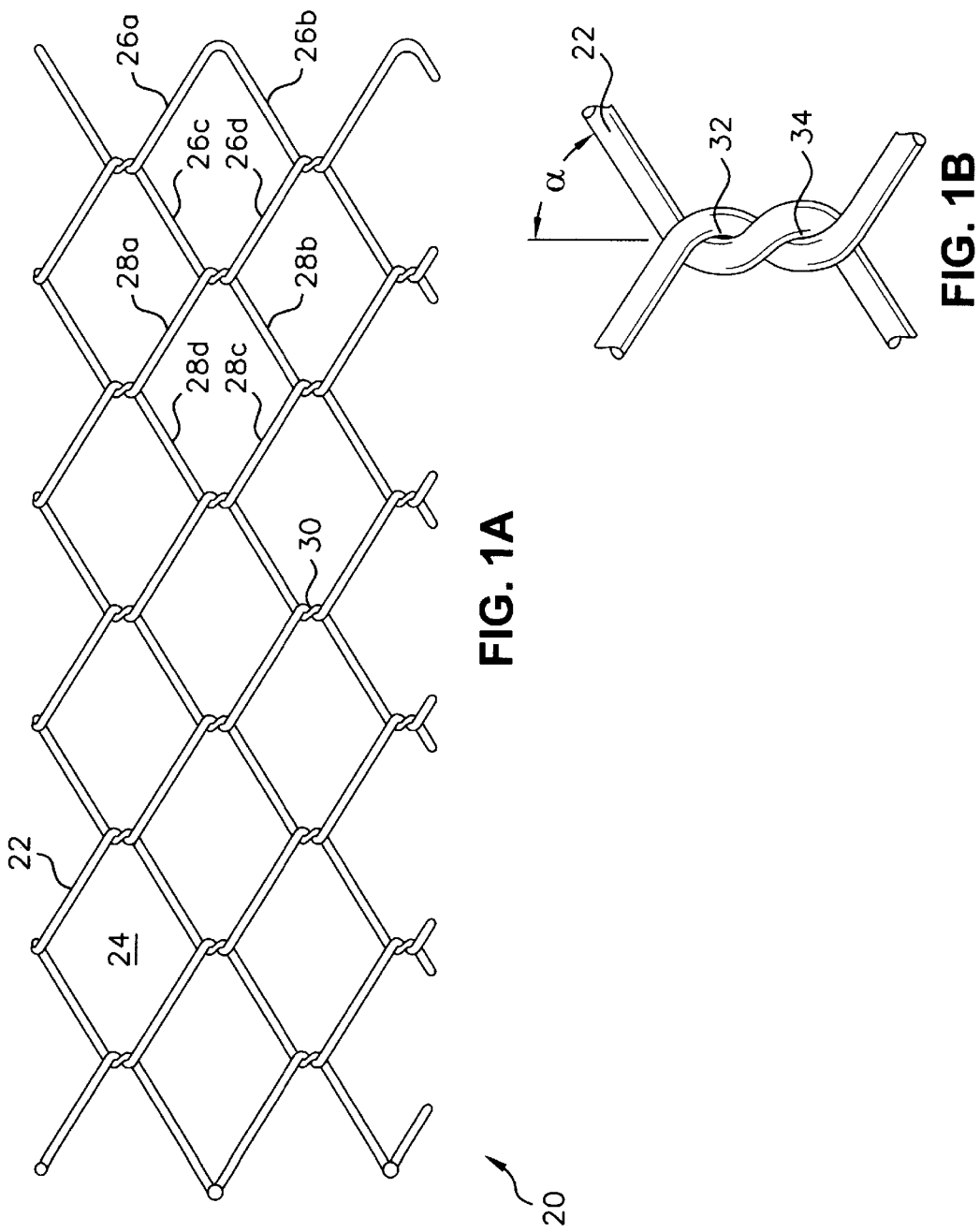

FIG. 2A
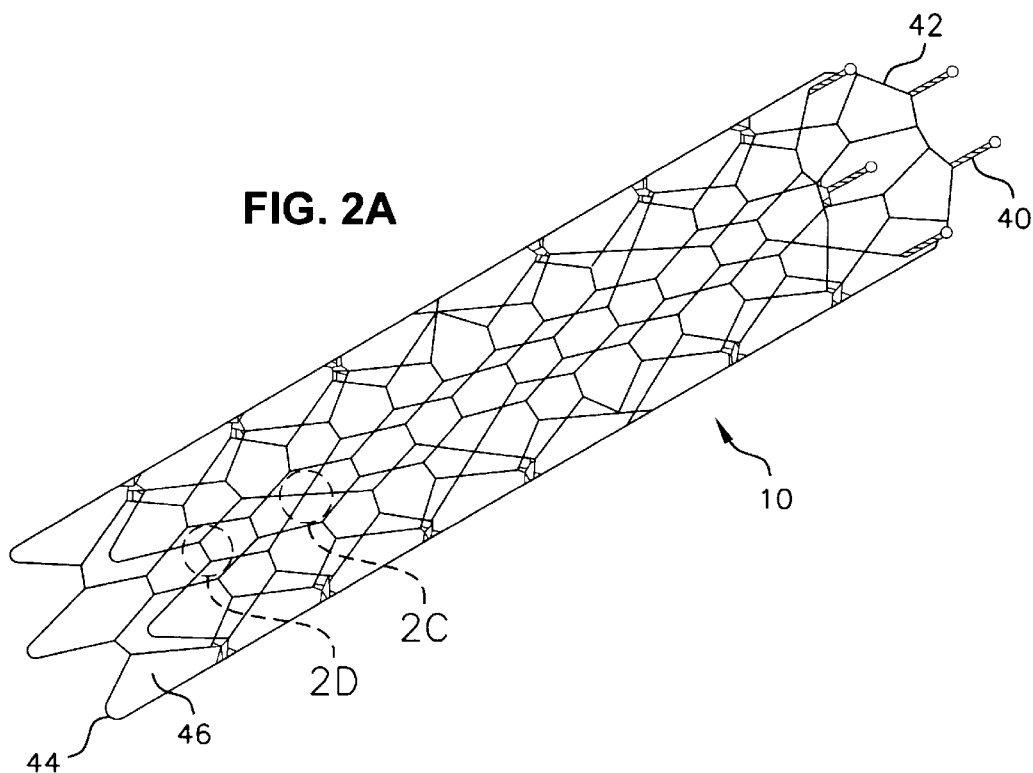
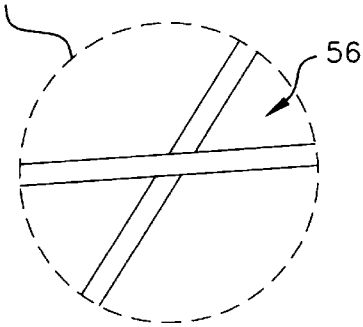
FIG. 2C
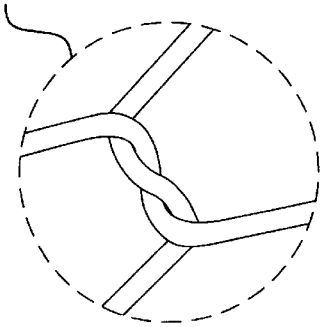
FIG. 2D

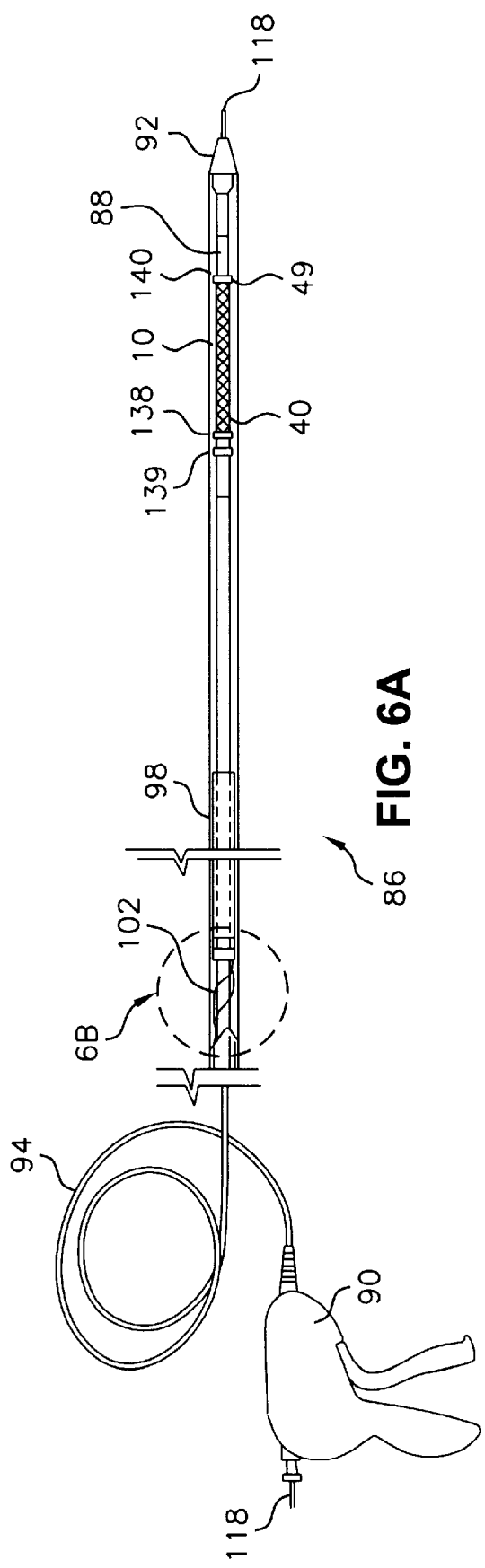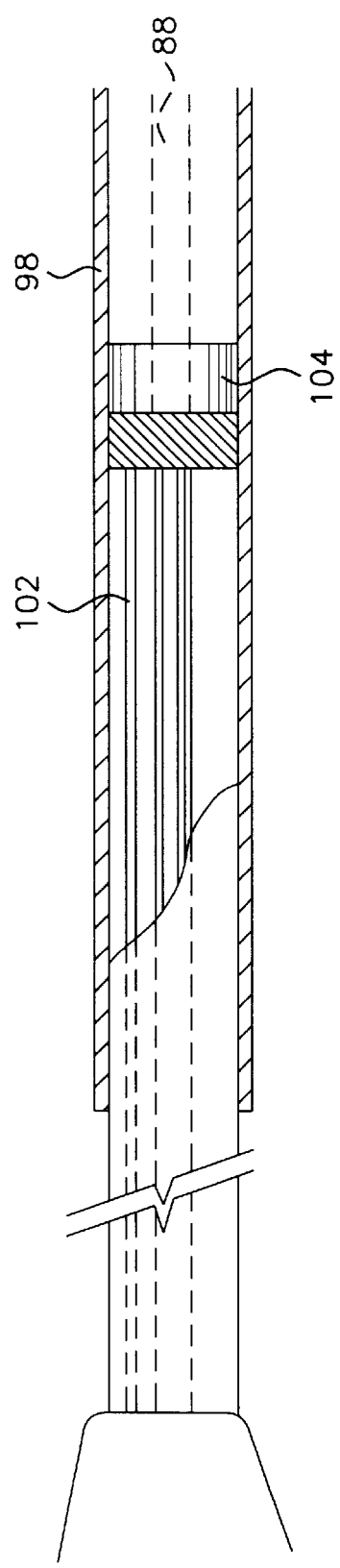
FIG. 6A
FIG. 6B

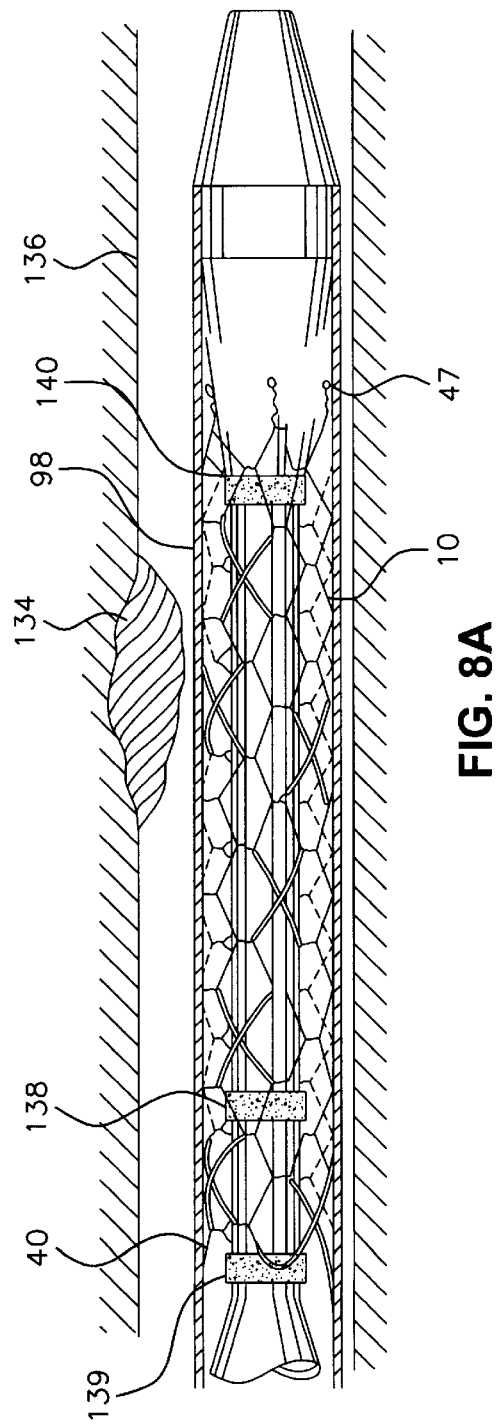
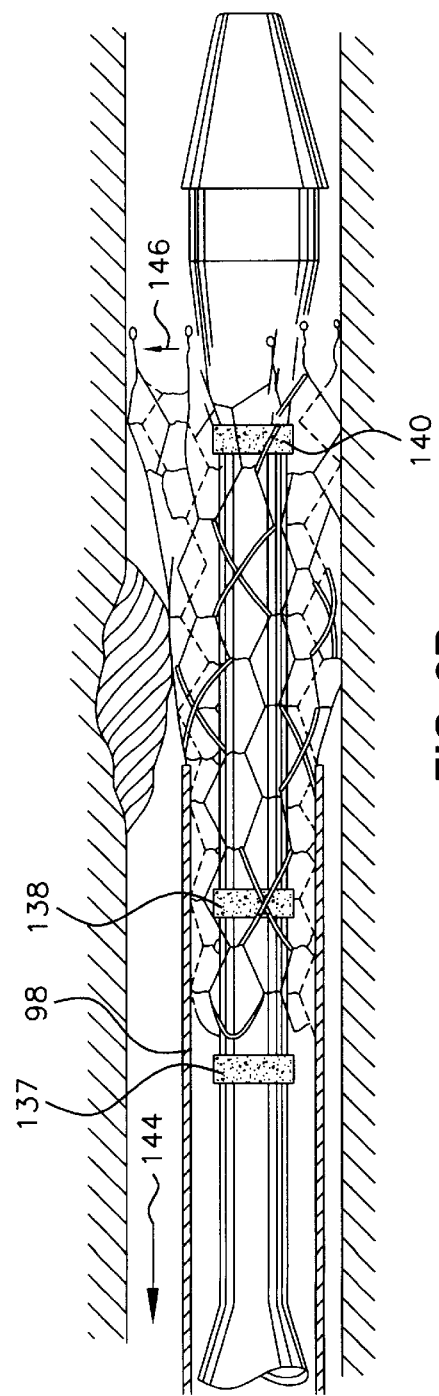
FIG. 8A
FIG. 8B

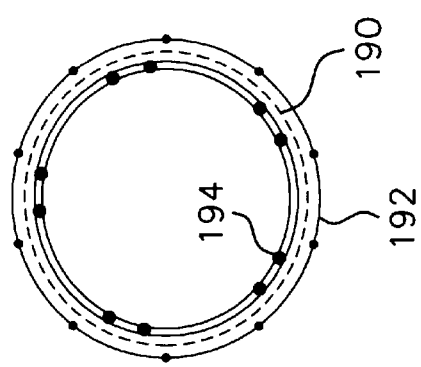
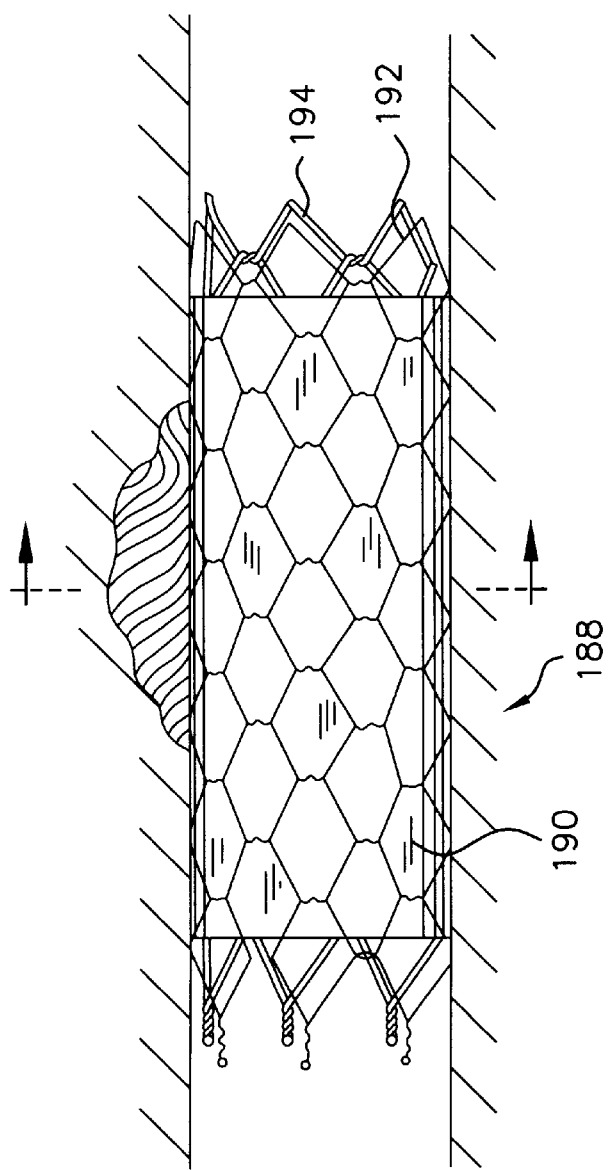

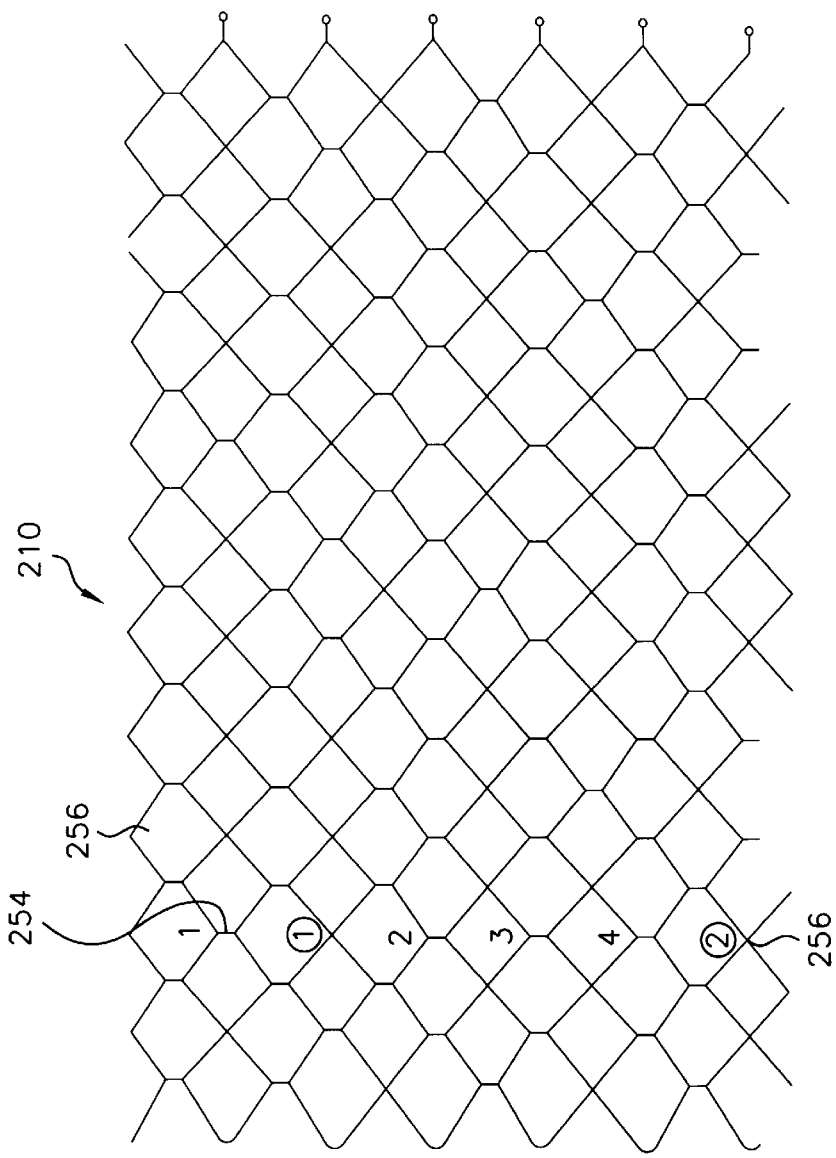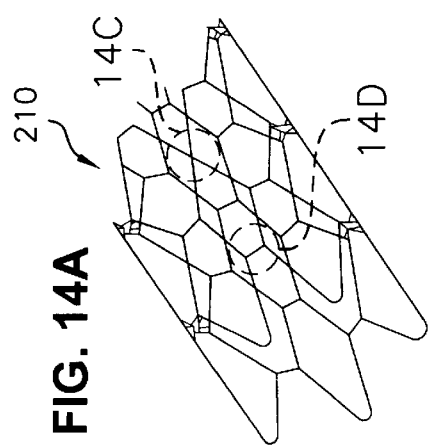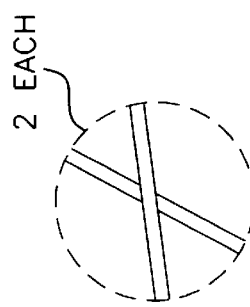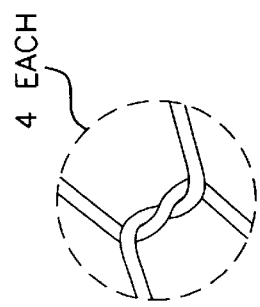

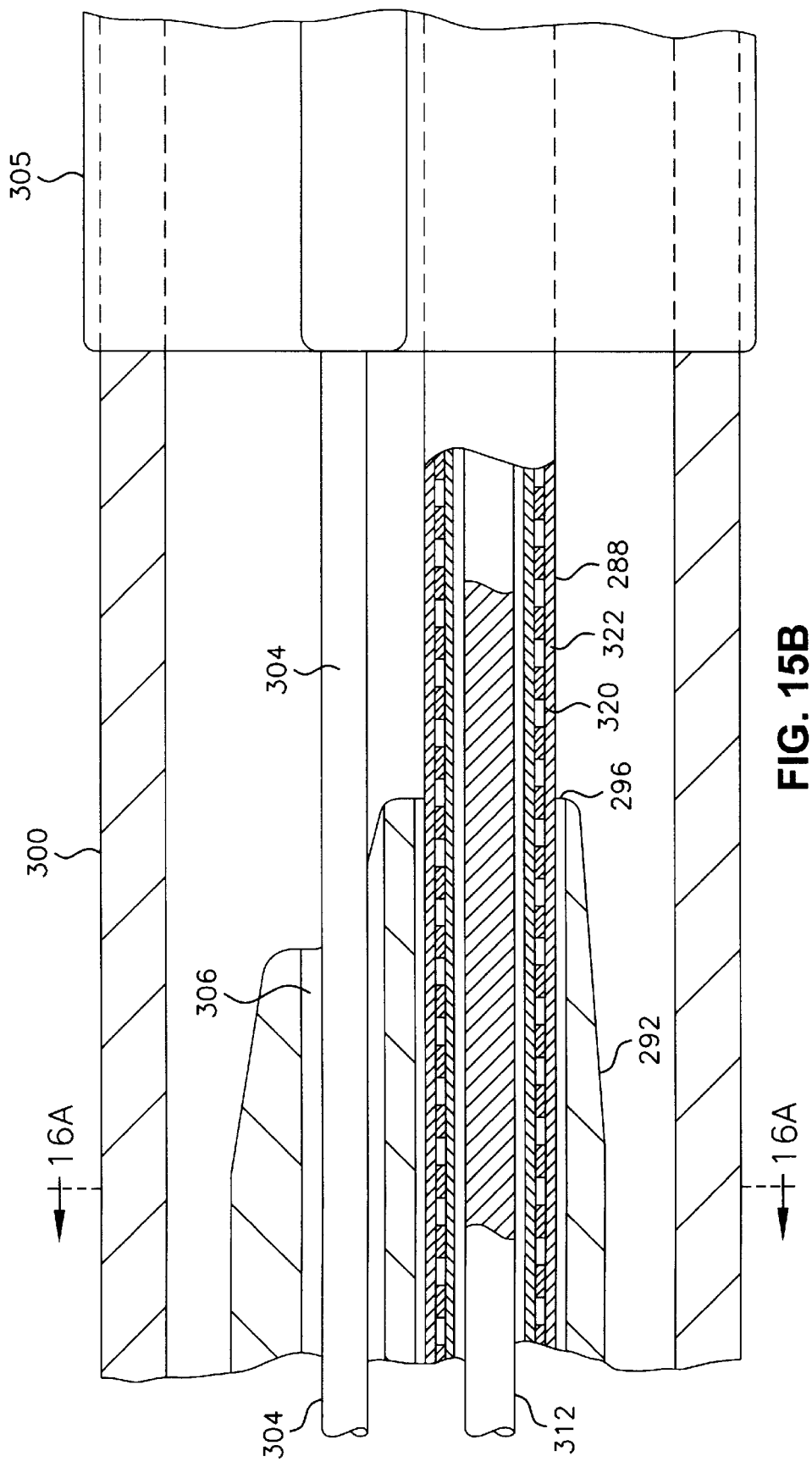

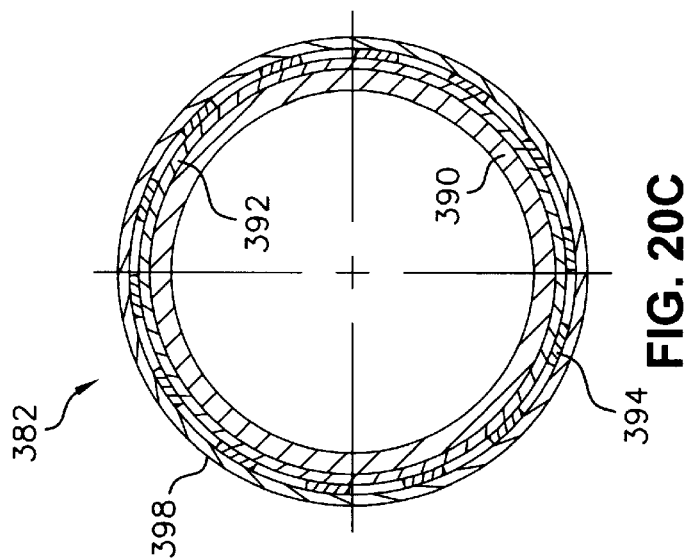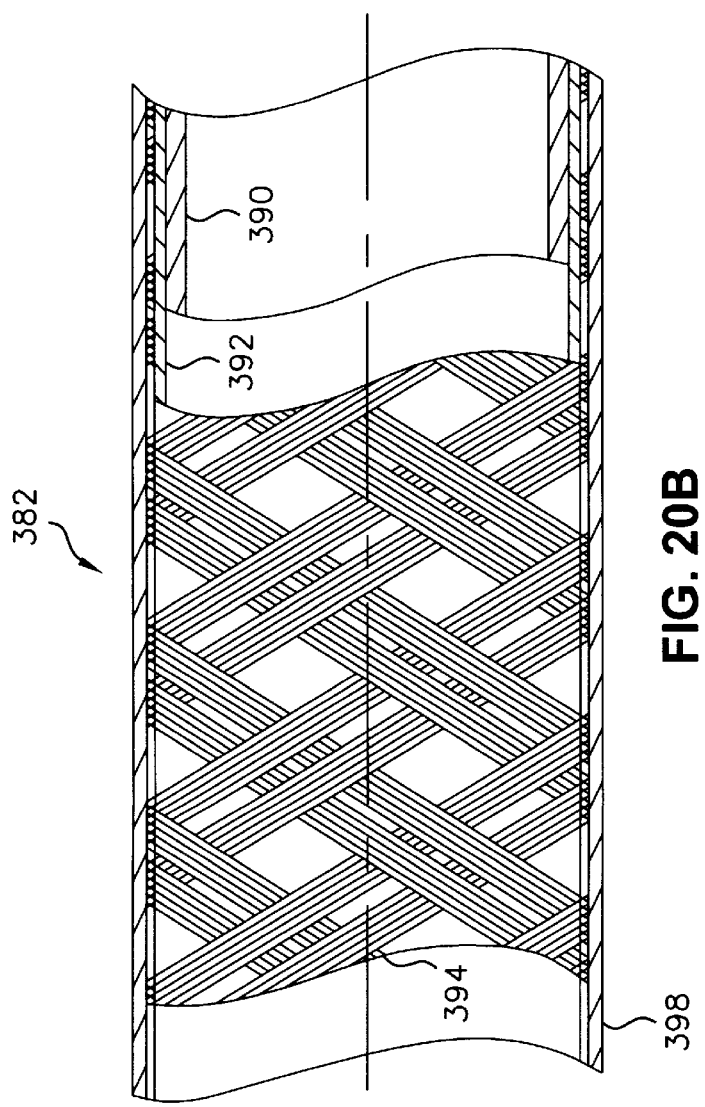

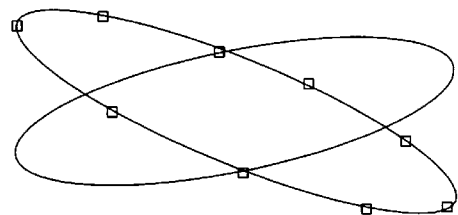
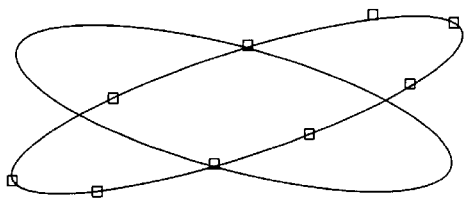
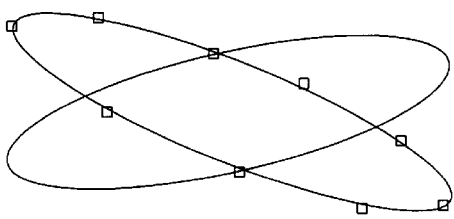
FIG. 24A
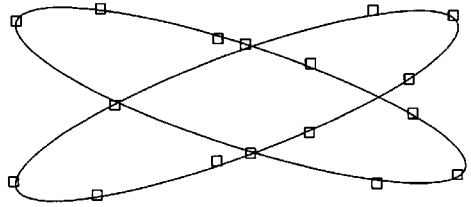
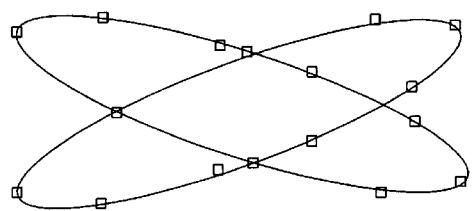
FIG. 24B

STENT DELIVERY SYSTEM

RELATED APPLICATION

This application is a continuation-in-part of U.S. patent application Ser. No. 09/052,214 filed on Mar. 31, 1998, the entire teachings of which are incorporated herein by reference.

BACKGROUND OF THE INVENTION

Implantable medical prostheses, such as stents, are placed within the body to maintain and/or treat a body lumen that has been impaired or occluded, for example, by a tumor. The stent can be formed of strands of material formed into a tube and are usually delivered into the body lumen using a catheter. The catheter carries the stent to the desired site and the stent is released from the catheter and expands to engage the inner surface of the lumen.

A self-expanding stent can be made of elastic materials. These are held in a compressed condition during catheter delivery by, for example, a sheath that covers the compressed stent. Upon reaching the desired site, the sheath constraining the stent is pulled proximally, while the stent is held in the desired position such that the stent expands.

There are both self-expanding and non-self-expanding stents. The self-expanding type of device is made with a material having an elastic restoring force, whereas a non-self-expanding stent is often made with elastic, plastically deformable material. It is positioned over a mechanical expander, such as a balloon, which can be inflated to force the prosthesis radially outward once the desired site is reached.

SUMMARY OF THE INVENTION

In a preferred embodiment, the invention features an implantable medical stent having a low profile during delivery. The stent is a tubular body with a body wall structure having a geometric pattern of cells defined by a series of elongated strands extending to regions of intersection. An example of a stent having a cell shape in accordance with the invention can be found in U.S. Pat. No. 5,800,519, which issued on Sep. 1, 1998, the entire contents of which is incorporated herein by reference. This stent cell structure utilized helically wrapped joints to connect the different strands to form a tubular body.

A limitation on the use of the helically joined stent involved the minimum constrained diameter of the stent during delivery. Because of the helically wrapped joints abutting one another along a given circumference, the minimum constrained diameter of the stent was 9 French (3 mm). For example, the length of the helically wrapped joint for a strand having a diameter of 0.006 inches (0.15 mm) in the constrained position is 0.045 inches (1.1 mm). For a five cell structure having five helically twisted abutting joints, this results in a constrained circumference of 0.228 inches (5.79 mm) with a diameter of 0.072 inches (1.8 mm). However, there are many applications in which it is necessary to achieve a smaller constrained diameter to provide delivery, for example, through smaller lumens within the vascular system, to reduce trauma during percutaneous delivery, or to provide endoscopic delivery through small diameter channels of endoscopes.

To achieve a smaller constrained diameter of 8 French or less, for example, a preferred embodiment of the invention replaces one or more of the helically wrapped joints along any given circumference with a simple crossed joint in which one strand crosses either above or below a second strand. Thus, the strands at a crossed joint can move more freely relative to each other, but this structure reduces the minimum circumference as the length of one or more helically twisted joints has been removed. This can reduce the constrained diameter by 50%.

In another preferred embodiment of the invention, the stent can include a first tubular body made from a first group of strands and a second tubular body surrounding the first tubular body and made from a second group of strands. This type of structure can be used to fabricate a low-profile device having sufficient radial expansion force for a self-expanding stent without a substantial change in foreshortening. This embodiment can include, for example, three or four helically wrapped joints along any circumference of the first and second tubular bodies in which the joints of the two bodies are offset in the constrained state. This embodiment also significantly improves the ratio of the expanded diameter to the constrained diameter.

The strands of the first group can have a different shape, diameter, or material from the strands of the second group such that the inner body has a larger radial restoring force than the outer body and can thereby impart the outward force to the outer body.

In one embodiment, the strands of the inner body can be thicker than the strands of the outer body and can be interleaved with the outer body along the entire length of the stent. In another preferred embodiment, the inner and outer bodies can be interlocked at one or both ends. This can permit the use of a cover between the inner and outer bodies along a certain portion of the stent. The use of the cover can enhance epithialization between the wall of the lumen and the outer body, reduce migration of the stent in certain applications and can prevent tumor in-growth. The cover can also provide a supporting matrix for drug delivery.

In one preferred embodiment, the strands of the stent are woven in a pattern with interlocking joints and skip joints as discussed above. In addition, the adjoining ends of the stent are aligned parallel to each other and laser-welded to secure the adjoining ends of the stent. The welded ends allow the stent to be compressed to a low profile.

In one preferred delivery system, the stent is positioned over an inner shaft and is covered by a composite sheath. The composite sheath can comprise a plurality of materials to provide a variable property such as a graded stiffness along the length of the sheath. In one embodiment the sheath can include a braid or coil between outer and inner sheath layers to provide the longitudinal stiffness and flexibility needed for particular applications. The sheath can have at least a ten percent variation in stiffness along its length and as much as a fifty percent variation with the stiffer section at the proximal end and the least stiff section at the distal end. The sheath can extend coaxially about the inner shaft from the handle connected to the proximal end of the catheter and can be connected to an actuator that is manually operated by the user to slide the sheath relative to the inner shaft.

In one embodiment the inner shaft can include a braided tube, which extends from the proximal handle to a distal position of the delivery system. The inner shaft extends through a lumen of a catheter from the proximal handle to a distance short of the distal end where the catheter ends. The inner shaft can be free-floating within the lumen and receives the stent at the distal end. An outer sheath overlies the stent and the inner shaft and is moved to release the stent using a pull wire which is moved by the proximal handle using a conventional tooth strip attached to a pull wire.

In a preferred embodiment, the inner shaft is formed of steel braided tube encased in a polyimide. For low profile stent delivery systems, where the smaller diameter of the body lumen or the smaller diameter of the endoscope delivery channel necessitate improvements in the push (or pull) strength of the catheter, the use of a braided tube to maintain flexibility and pushability without kinking provides effective delivery of low profile stents.

In the embodiments described above and in other embodiments, a mounting ring can be secured to the inner shaft or braided tube at the stent platform on which the stent is placed. The mounting ring has at least one radial member or ridge which projects towards the outer sheath. The ridge is located preferably at the proximal end of the stent. The ridges extend longitudinally, allowing the stent to be properly positioned while also allowing maximum compression of the stent for minimizing the diameter of the delivery system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A is a flat layout view along the longitudinal axis of a stent;

FIG. 1B is an enlarged portion of the stent taken at section 1B—1B in FIG. 1A;

FIG. 2A is a perspective view of a stent according to the invention;

FIGS. 2C and 2D are close-up views of their respective portions as shown in FIG. 2A;

FIG. 6A is an "over-the-wire" delivery system;

FIG. 6B is an enlarged view of the middle section of the "over-the-wire" delivery system;

FIGS. 8A–8E illustrate the operation of the delivery of the stent;

FIG. 11 is an enlarged cross sectional view of the double layer stent of FIG. 10 with an interposed cover in an artery;

FIG. 12 is a cross sectional view of the double layer stent with the interposed cover taken along line 12—12 of FIG. 11;

FIG. 14A is a perspective view of an alternative stent having six strands; and

FIG. 14B is a flat layout view of the stent of FIG. 14A.

FIGS. 14C and 14D are close-up views of their respective portions as shown in FIG. 14A;

FIG. 15B is an enlarged view of a middle section of an "over-the-wire" delivery system;

FIG. 20B is a similar view with the inner shaft removed;

FIG. 20C is a sectional view of the distal end of an "over-the-wire" delivery system.

FIGS. 24A and 24B are oblique views of the nodes of a stent;

DETAILED DESCRIPTION OF THE INVENTION

Figure 2B:
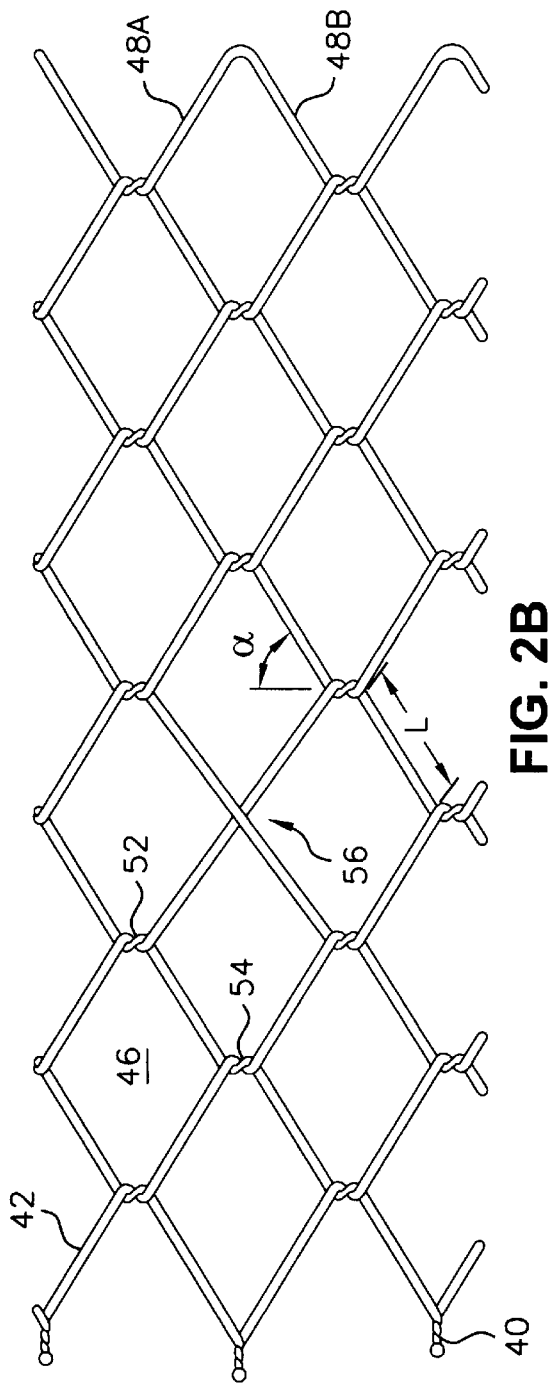
FIG. 2B is a flat layout view of an expanded low profile stent of FIG. 2A.

Referring to the drawings in detail, where like numerals indicate like elements, there is illustrated an implantable prosthesis in accordance with the present invention designated generally as 10.

Medical prostheses, such as a stent 10 according to the invention, are placed within the body to treat a body lumen that has been impaired or occluded. Stents according to the invention are formed of wire configured into a tube and are usually delivered into the body lumen using a catheter. The catheter carries the stent in a reduced-size form to the desired site. When the desired location is reached, the stent is released from the catheter and expanded so that it engages the lumen wall as explained below.

A stent 20 is shown in a flat layout view in FIG. 1A. The stent 20 is formed of elongated strands 22 such as elastic metal wires. The wires 22 are woven to form a pattern of geometric cells 24. The sides 26a, 26b, 26c, and 26d of each of the cells 24 are defined by a series of strand lengths 28a, 28b, 28c, and 28d. Each of the sides 26 are joined to the adjoining side at an intersection where the strands 22 are helically wrapped about each other to form interlocking joints 30.

Referring to FIGS. 1A and 1B, the interlocking joints 30 are loose and spaced from each other in the full expansion position. The cells 24 have a diamond shape. The strand angle is α. When the stent 20 is radially compressed, in certain instances, the interlocking joints 30 are in tight interference such that points 32 and 34 are in close proximity. In other instances, the interlocking joints 30 separate. In addition, the interlocking joints 30 on the same circumference are in close contact, therefore establishing the compressed, reduced size which can be fit within a sleeve for delivery on a catheter. A medical prosthetic stent and method of manufacturing such a stent is described in U.S. patent application Ser. No. 08/743,395 which issued as U.S. Pat. No. 5,800,519 on Sep. 1, 1998 and which is incorporated herewith by reference.

Referring to FIG. 2A, an isometric view of stent 10 according to the invention is shown in an expanded position. The stent 10 is formed from a plurality of strands 42. FIGS. 2C and 2D show enlarged views of two parts of the stent shown in FIG. 2A. In a preferred embodiment, there are five strands 42, as seen in the layout view of FIG. 2B. The strands 42 are woven in a pattern starting at a proximal end 44. The pattern forms a plurality of geometric cells 46. Each strand 42 forms a pair of sides 48a and 48b of the most distal cell 46. Each of the sides, with the exception of at least one as explained below, are joined to the adjoining side at an intersection 52 where the strands 42 are helically wrapped about each other to form interlocking joints 54.

While there are five intersections 52, at least one of the intersections 52 is formed by strands 42 that cross forming a cross joint and are not twisted to form a wrap as indicated at point 56 in FIG. 2B. A preferred pattern of where the strands 42 just cross is spaced 1-½ cells 46 away, as seen in FIG. 2B.

The strand angle α is increased in the compressed or constrained state of the stent in this embodiment. The strand angle can be in the range of 10°–80° depending upon the particular embodiment. Smaller strand angles between 10° and 45° often require a shortened cell side length L to maintain radial expansion force. Cell side lengths L in the range of 0.5 to 4 mm, for example, can be used with stent having these smaller strand angles. For stents with larger strand angles in the range of 3–8 mm can be used, depending on the expanded diameter of the stent, the number of cells and the desired radial expansion force.

Figure 3:
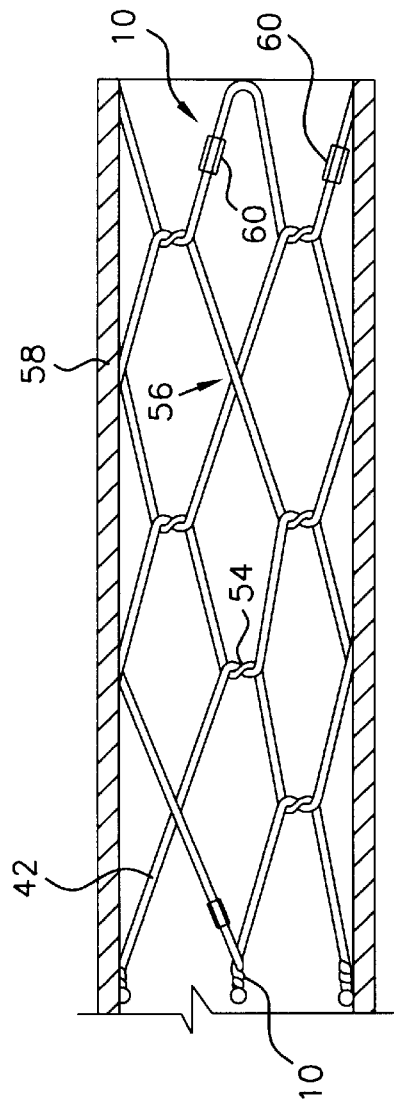
FIG. 3 is an enlarged cross-sectional view of a delivery tube containing a low profile diamond metal stent.

Referring to FIG. 3, the stent 10 is shown in the contracted position within the sleeve 58. Similar to the embodiment shown in FIGS. 1A and 1B, the size to which the stent 10 can be constricted is limited by where the interlocking joints 54 engage each other. The elimination of one wrap joint allows for the stent 10 to be compressed to a smaller size.

In a preferred embodiment, the strands 42 are formed of nitinol wire. The wires each have a diameter of 0.006 inches (0.15 mm). The diameter of the wires can vary depending on the number of cells and desired properties and generally in preferred embodiments range from 0.004 inches (0.10 mm) to 0.006 inches (0.15 mm). The stent 10 has an outside diameter when fully expanded of 10 millimeters. The stent 10 is capable of compressing into a sleeve 58 of an outside diameter of 8.0 French or less, and preferably 7.0 French (3 fr=1 mm). The stent shown in the FIGS. 1A and 1B, of similar material and dimension, is capable of compressing to a diameter of approximately 9 fr.

In one preferred embodiment, the length of the legs or sides 48 of the cells 46 is similar to that of the embodiment shown in FIGS. 1A and 1B. The radial force is decreased from the elimination of one of the interlocking or wrap joints. The compressed stent 10 has a length of approximately 120 percent or less relative to the expanded stent. Therefore, for a 10 centimeter stent, the compressed length is 12 centimeters or less.

In one preferred embodiment, the length of the legs or sides 48 of the cells 46 are reduced. The reduced length provides radial force and compensates for decreased radial force resulting from the elimination of one of the interlocking or wrap joints. In an alternative embodiment, the radial expansion force increased by varying the anneal cycle of the stent.

The varying of the length of legs or sides 48 of the cell or the change in the angle α can effect foreshortening. While it is preferred to have foreshortening of 120 percent or less, in certain embodiments it may be desirable to have greater foreshortening, such as the compressed stent 10 has a length of approximately 150 percent of the expanded stent.

In one preferred embodiment, a plurality of (ten shown) platinum-iridium radiopaque (R.O.) markers 60 are located on the stent 10. The R.O. markers 60 are threaded onto the terminating cells; five on the proximal end and five on the distal end.

Figure 4A:
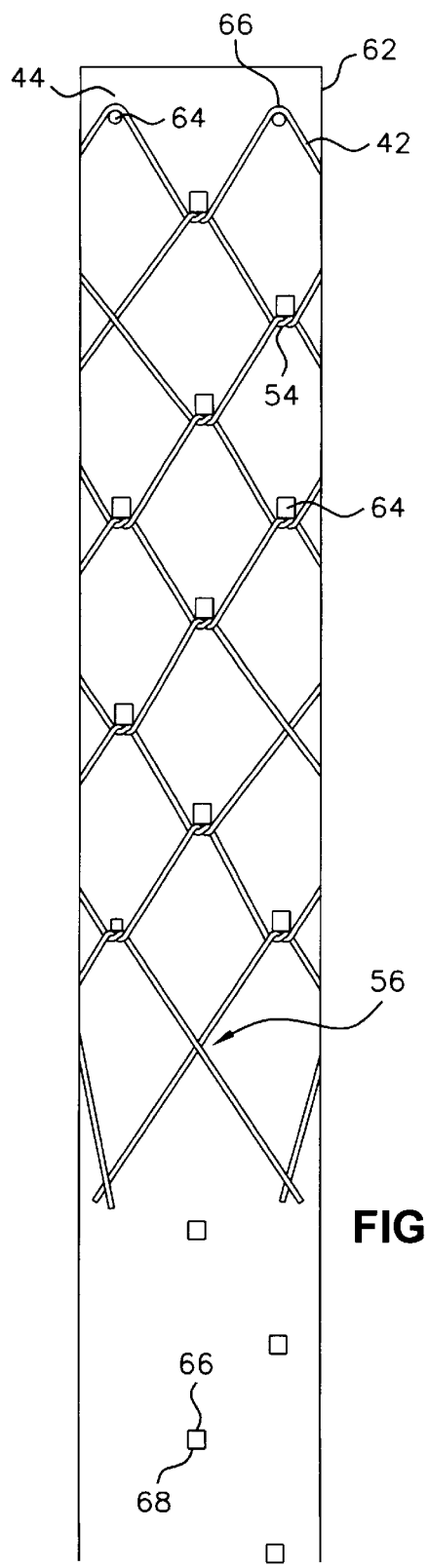
FIGS. 4A and 4B illustrate a mandrel for making a stent of FIGS. 2A, 2B, and 3.
Figure 4B:
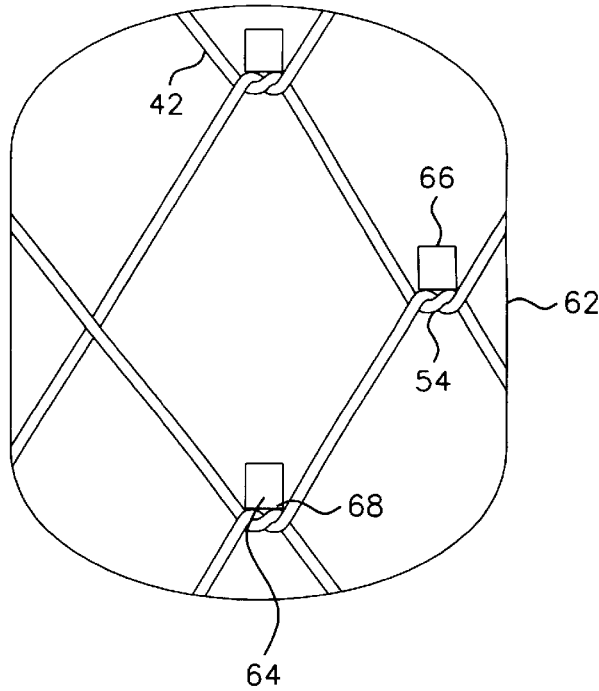

A mandrel 62 for making the stent is shown in FIGS. 4A and 4B. The mandrel 62 has a plurality of pins 64 on the outer surface of the mandrel in a pattern that determines the geometric cell 46 pattern. The strands 42 are bent around the top portion 66 of each top anchoring pin 64 to form the proximal end 44 of the stent 10. The strands 42 are then pulled diagonally downward to an adjacent anchoring pin 64 where the strands 42 are joined. The strands 42 are helically wrapped about each other to form the interlocking joint 54, with each strand passing through a single 360 degree rotation. The two strands are pulled taught so that the interlocking joint 54 rests firmly against the bottom portion 68 of the anchoring pin 64 such that each strand 42 is maintained in tension.

Each level of anchoring pins 64 is missing a pin 64 in a set order, such as to achieve the desired pattern in FIG. 2B.

The stands 42 which pass the missing pin location simply cross to form the cross joint.

In a preferred embodiment, the anchoring pins 64 are square. The square pins retain the helically wrap of the strands in a proper position. In a preferred embodiment, the pins have a width of 1 millimeter. The anchoring pins can have a smaller width such as 0.5 mm for use with narrower diameter strands, such as 0.005 inch diameter strands.

The free ends of the strands 42 are then pulled downward to the next diagonally adjacent anchoring pin 64. This process is continued until the desired length of the stent 10 is achieved.

Figure 4C:
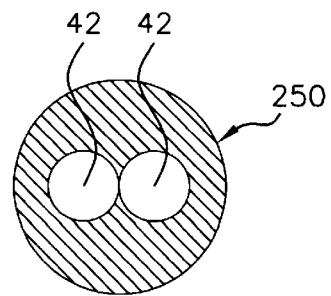
FIG. 4C is a sectional view of the strands attached with a ball-welding.

The stent 10 is then heat-treated. The strands 42 at the joining end 40 of the stent 10 are welded using a ball-welding technique. The strands 42 are twisted around each other for several twists of the strands as best seen in FIG. 2B. The strands having a diameter of 0.006 inches (0.15 mm) will form a diameter of 0.012 inches as seen in FIG. 4C. In addition, the ball-weld creates a weld ball 250 having a diameter of 0.018 inches (0.46 mm) to 0.020 inches (0.51 mm). Upon compression of the stent, the weld balls 250 may engage each other limiting the compression of the stent. The stent with these diameters can fit within an outer sheath having a 7 French inner diameter. The heat-treating and alternative finishing techniques are described in U.S. Pat. No. 5,800,519 on Sep. 1, 1998, the entire contents is incorporated herein by reference.

Figure 4D:
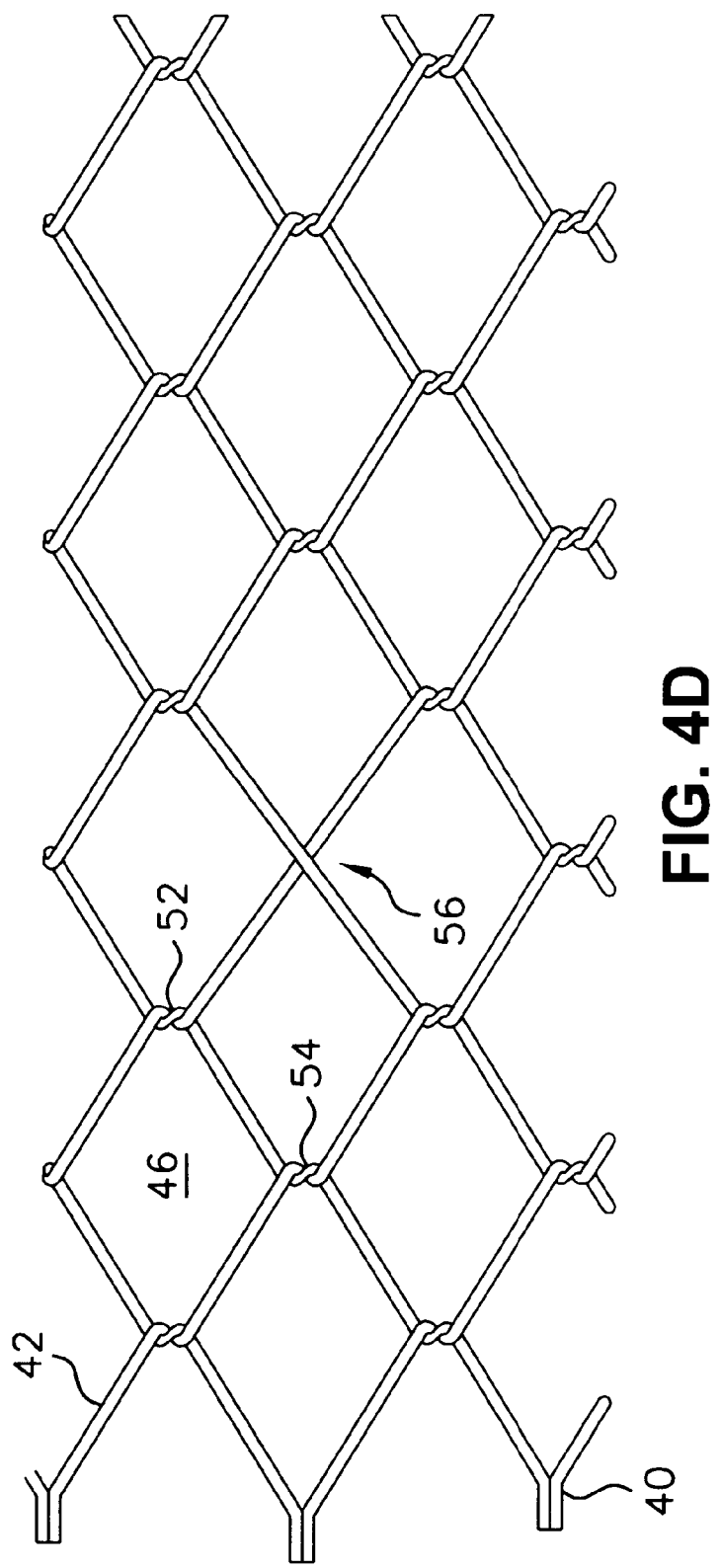
FIG. 4D is a flat layout view of the joining ends of a low profile stent according to an alternative embodiment.
Figure 4E:
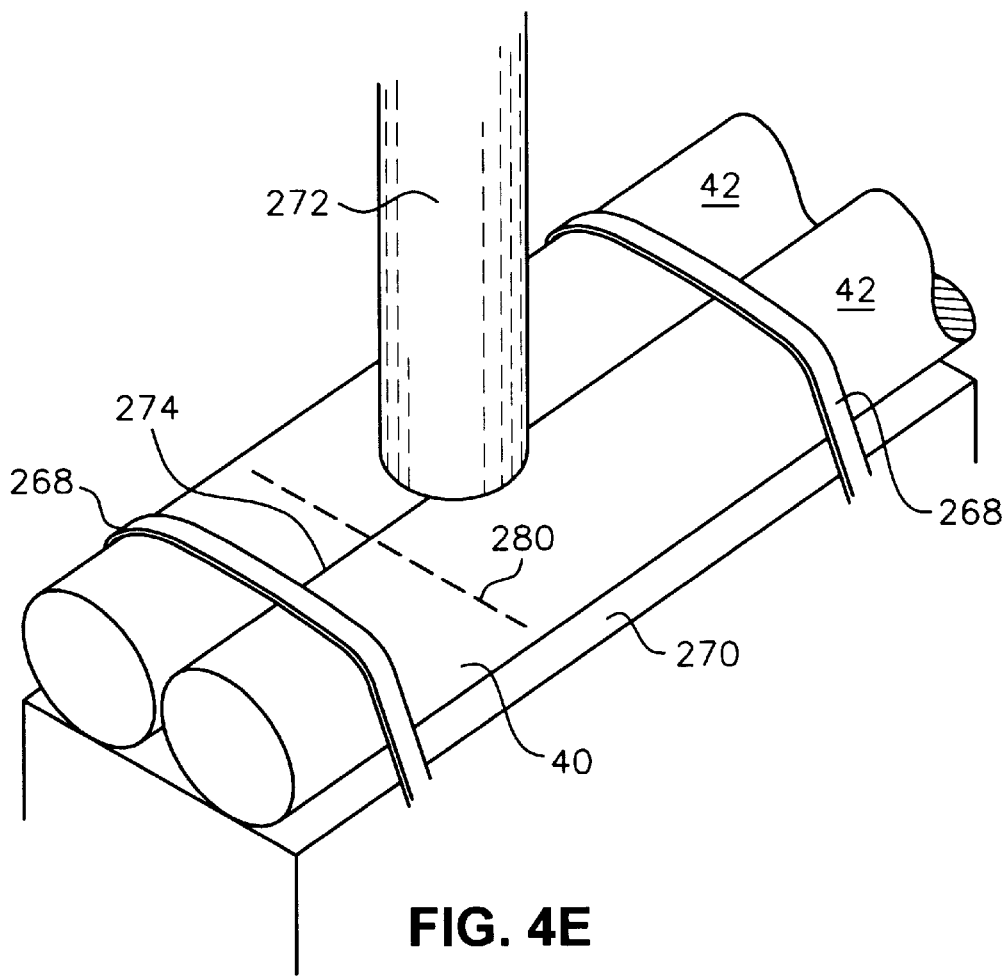
FIG. 4E is a perspective view of the strand of the stent in a laser welding apparatus.

A layout view of the distal end of the stent 10 is shown in FIG. 4D. The strands 42 of the stent 10 are woven in a pattern as discussed above with respect to FIGS. 4A and 4B. The joining ends 40 of the stent 10 are aligned parallel to each other to form the end of the most distal cells 46. The joining ends 40 of the strands 42 are held together by a pair of holding straps 268 onto a surface 270 as seen in FIG. 4E. A laser welder 272 moves along the joint 274 of the two adjoining strands 42. A plurality of energy pulses are directed at the joint 274 as the laser welder 272 moves along the joint. After completing this initial weld, the laser welder 272 is moved back to a position 280, to achieve a finished length and a higher energy pulse is directed at the point or position mark by dotted line 280 to cut the strands 42.

In a preferred embodiment, a 400 micron fiber is used with a spot size having a diameter of 3.9 to 4.1 millimeters. In one example, twenty pulses of energy are directed at the joint 274 as the laser welder 272 moves a distance of 1.3 millimeters (+/−0.5 mm). Each pulse has an energy level of 145 millijoules (+/−10 millijoules) and a duration of 0.1 milliseconds. The single higher energy pulse of one joule, and a duration of 2 milliseconds cuts the strands.

Figure 4F:
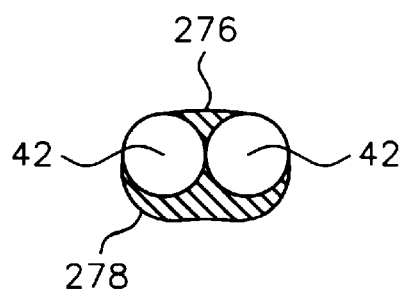
FIG. 4F is a sectional view of the strands laser welded.

Referring to FIG. 4F, an example of the cross-section of the strands 42 using the laser weld technique described above is shown. The laser welding forms a fill 276 on the top and a cut-off fill 278 on the bottom. The overall diameter of the strands 42 and weld is 0.012 inches (0.3 mm)therein for a five wire system the compression size is 4.57 French. Therein, a stent with the laser welded ends can compress to a smaller diameter than those with the ball welds.

Another alternative to the R.O. markers 60 for locating the stent 10 using fluroscopy is to coat the stent with gold. The stent 10 can be either totally or partially coated. In a partially coated stent, only portions of the strands between the joints are coated. Coating of a stent is described in further detail in U.S. Pat. No. 5,201,901 which issued on Apr. 13, 1993, the entire contents is incorporated herein by reference. A clad composite stent is described in U.S. Pat. No. 5,630,840 which issued on May 20, 1997, the entire contents being incorporated herein by reference. A further embodiment of the invention utilizes a stent having a core as described in U.S. Pat. No. 5,725,570 which issued on Mar. 10, 1998, the entire contents is incorporated herein by reference.

Figure 5B:
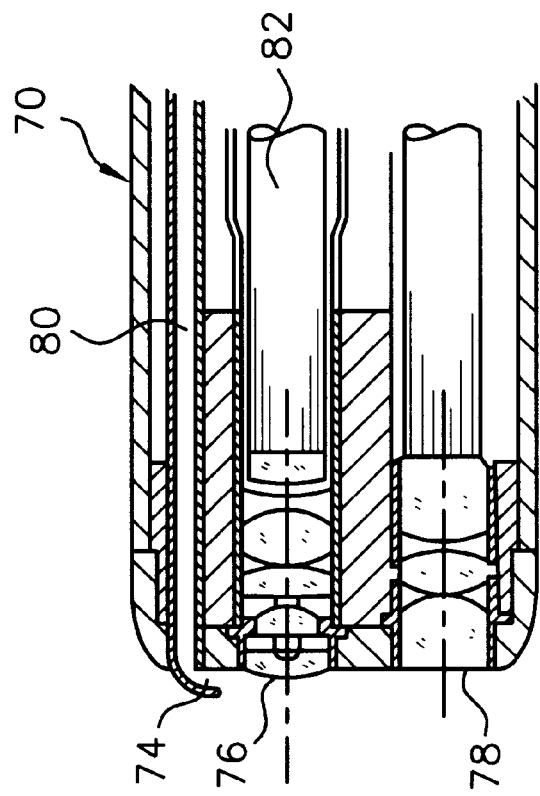
FIG. 5B is a sectional view of the distal end of the endoscope.
Figure 5A:
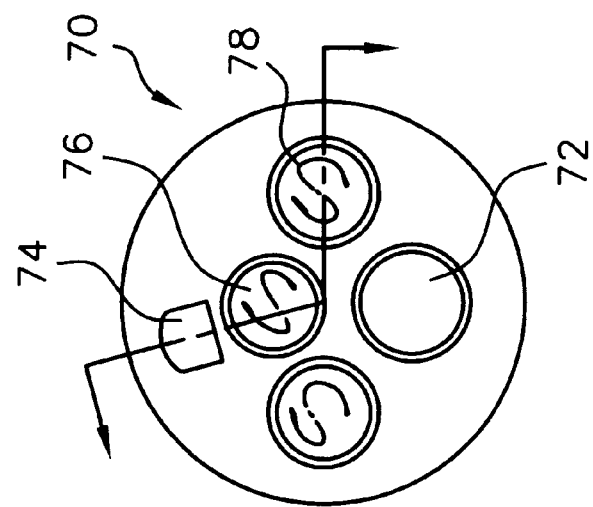
FIG. 5A is a distal end view of an endoscope.

In one preferred embodiment, the stent 10 is installed using an endoscope 70 as seen in FIGS. 5A and 5B. The endoscope 70 has a channel 72 which is typically used for collecting biopsy samples or for suction. The stent 10 is passed through the channel 72 into the body as explained below. The endoscope 70 in addition has an air/water nozzle 74 for cleaning the area in front of the endoscope 70. In addition, the endoscope 70 has a mechanism for the physician to see what is in front of the endoscope 70; this mechanism includes an objective lens 76. A pair of illumination lenses 78 which are used in lighting the site are also shown.

FIG. 5B illustrates a cross sectional view of the distal end of the endoscope 70. An air/water tube 80 extends down to the air/water nozzle 74. Both the viewing mechanism and the illumination mechanism have optical fiber bundles 82 leading to the respective lens 76 and 78.

Endoscopes come in various sizes and lengths depending on the purpose. The channel 72 likewise has different sizes. It is recognized that it may be desirable to use a smaller diameter scope to be less invasive or that a larger diameter scope will not fit the lumen. The following table is an example of various size endoscopes.

| Working Length (cm) | Distal Tip O.D. (mm) | Channel Diameter (mm) |
| --- | --- | --- |
| 55 | 4.8 | 2.0 |
| 55 | 6.0 | 2.6 |
| 63 | 12.2 | 3.2 |
| 102 | 9.8 | 2.8 |
| 102 | 12.6 | 3.7 |
| 124 | 11.0 | 2.8 |
| 124 | 11.0 | 3.2 |
| 125 | 11.3 | 4.2 |
| 173 | 13.0 | 3.2 |

In a preferred embodiment, with the dimensions given above, the stent 10 as described in relation to FIGS. 2A–4B can be used with channels of 3.2 mm or greater as described below. It is recognized that with other dimensions of the stent and/or laser weld of the ends, the stent catheter can fit in a smaller diameter channels such as 2.6 mm or 2.0 mm. For a 2.6 mm endoscope channel, a 2.3 mm outer shaft or catheter diameter is employed.

In addition, the stent 10 can be introduced using a percutaneous insertion. In both the method using the endoscope 70 and the percutaneous procedure, an over the wire delivery system 86 as seen in FIG. 6A can be used. The over-the-wire delivery system 86 has an elongated catheter on inner shaft 88 over which the stent 10 is positioned. The shaft 88 extends from a proximal handle 90 to a distal tip end 92. The shaft 88 extends through an outer shaft 94 at the proximal end.

An outer sheath 98 is located at the distal end of the over the wire delivery system 86. The outer sheath 98 is moved towards the handle 90 using a pull wire 102 and a pull ring 104 as seen in FIG. 6B. A guidewire 118 extends through the catheter to the distal end tip 92, as best seen in FIG. 6A.

In a preferred embodiment, the outer sheath 98 has an outer diameter in the range of between 0.072 inches (1.8 mm) and 0.094 inches (2.4 mm). The inner diameter of the outer sheath 98 has a range of between 0.066 inches (1.7 mm) and 0.086 (2.2 mm)inches. The outer sheath tends to the lower portion of the range when the stent can contract to the 6 French size and towards the upper portion of the range when the stent can contract to the 7 French size.

In one preferred embodiment, the outer sheath 98 is formed having several layers of material. The nominal outer diameter is 0.093 inches and a nominal inner diameter of between 0.078 and 0.081 inches. The inner layer is composed of polyethylene or TFE and has a nominal thickness of 0.001 inches. A layer of EVA or polyurethane of a nominal thickness of 0.0005 inches forms the second layer. A braid metal spring stainless or liquid crystal polymer (LCP) fiber having a thickness of 0.0015 to 0.0025 inches overlies the second layer and forms the core of the outer sheath 98.

In a preferred embodiment, the fourth layer varies in material composition as it extends from the proximal end to the distal end. The proximal end of the sheath is formed of Pebax or polyamide and the material varies to a polyamide or cristamid at the distal end. This layer has a nominal thickness of 0.002 inches. This varying of the material is for increased flexibility at the distal end to move through tortures easier and increased rigidity at the proximal end to give the catheter better push.

The sheath 98 has a finish layer of a hydrophlic coating having a thickness of between 0.0005 and 0.001 inches. The coating is for increase lubricativity.

The shaft has an outer diameter of 0.074 inches (1.88 mm). The shaft is formed of nylon 12, or cristamid.

In a preferred embodiment, the tip extrusion has an outer diameter in the range of between 0.042 and 0.055 inches. The inner diameter of the tip extrusion has a range of between 0.036 and 0.040 inches.

In one preferred embodiment, the tip extrusion or catheter has a nominal outer diameter of 0.047 inches and an inner diameter of 0.037 inches. The inner diameter defines the passage for the guidewire. In a preferred embodiment, the catheter is formed of Peek (Polyether ether ether Keetone) Peek Braid Peek, Polyimide or Polyimide Braid Polyimide. In a preferred embodiment, the guide wire 108 has a diameter of 0.035 inches. It is recognized that the guide wire can be larger or smaller as indicated below.

Figure 7:
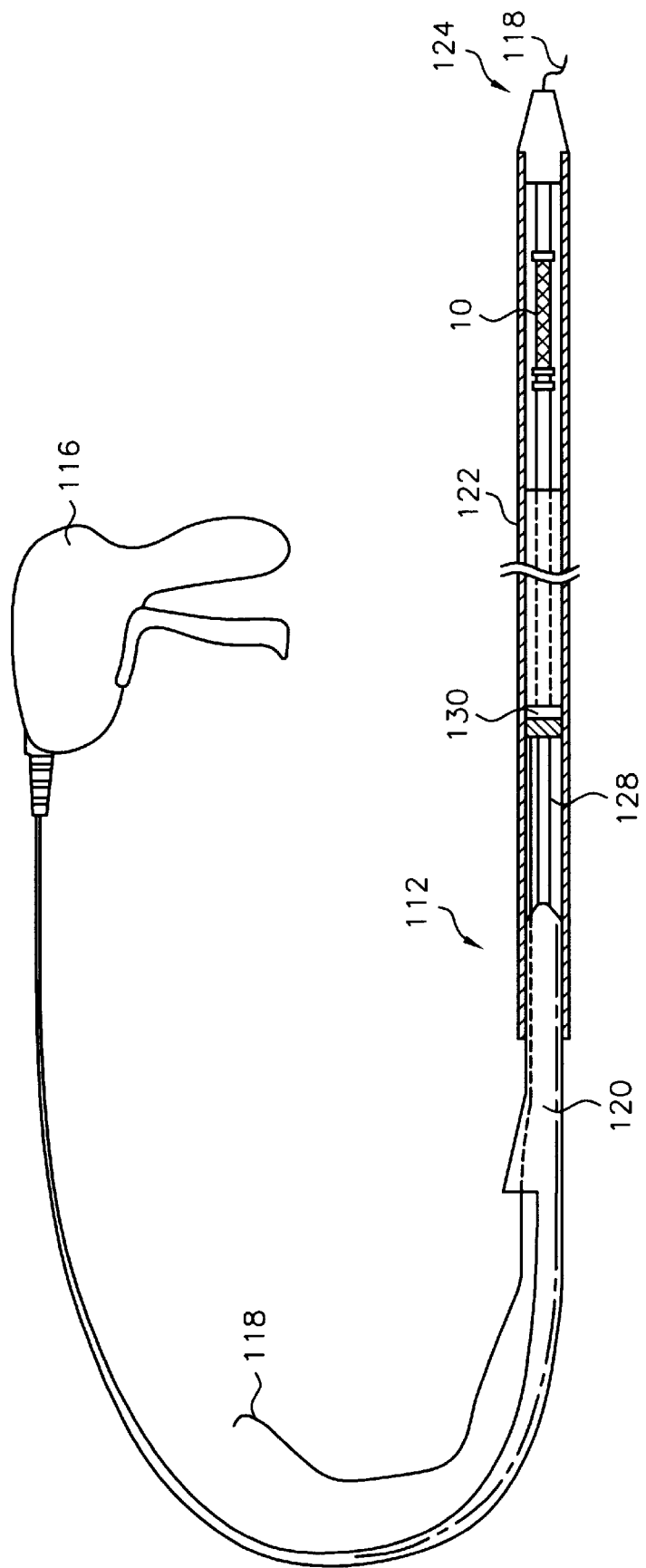
FIG. 7 is a rapid exchange delivery system.

An alternative method to the over-the-wire delivery system 86 shown in FIGS. 6A and 6B is a rapid exchange delivery system 112 shown in FIG. 7. The rapid exchange delivery system 112 has a shaft 114 that extends from a proximal handle 116. A guidewire 118 extends from a two lumen transition zone 120 through an outer sheath 122 to a distal tip end 124. In contrast to the over the wire delivery system 86, the guide wire 118 does not extend all the way back to the proximal handle 116. Similar to the over the wire delivery system 86, the outer sheath 122 of the rapid exchange delivery system 112 is moved towards the handle 116 using a pull wire 128 and a pull ring 130.

Referring to FIGS. 8A–8F, the over-the-wire delivery system 86 of FIGS. 6A and 6B is shown for positioning a stent 10 in a bile duct. Stents are used in many uses including for treatment of an obstruction 134, such as a tumor in the bile duct. The delivery system can position a prosthesis, such as a stent 10, to move the obstruction out of the lumen 136.

Typically, the occlusion substantially closes off a lumen, such as a bile duct which has a healthy diameter of about 8–10 mm. The obstruction may be several centimeters in length. After the obstruction is located using one of several diagnostic techniques, the physician gains access to the lumen. Using ultrasound or fluoroscopy, the guidewire 108 such as seen in FIG. 8C, is positioned through the outer access sheath 98 so that it extends past the obstruction.

Referring to FIG. 6A, the delivery system 86 is advanced axially and distally until the distal radiopaque marker 140 is positioned axially at a location at least about 1 cm distal of the occlusion 134. This location substantially corresponds to the position at which the distal end 47 of the stent 10, when expanded, will engage the lumen wall 136. The location is selected so the stent 10 is positioned beyond the occlusion 134 but not too close to the end of the bile duct, for example. The marker 138 indicates the position of the proximal end 40 of the stent 10 in the expanded position and is such that the proximal end 40 of the prosthesis will engage healthy tissue over a length of at least 1 cm. Where possible the stent 10 is centered about the obstruction, based on the fully expanded length indicated by markers 138 and 140. The marker 139 indicates the proximal end of tile stent when the stent is in the fully compact form, which has an overall length of approximately 20 percent longer than in its expanded state. Therefore for a stent of 7.5 centimeters, the compressed state has a length of approximately 9 centimeters.

The sheath 98 is retracted in one continuous motion as illustrated in FIG. 8B. With the sheath 98 partially withdrawn, (arrow 144), portions of the stent 10 expand (arrow 146). The lengthening of the stent 10 has a simultaneous effect of reducing the radial force the stent exerts on the wall of the sheath 98 and, therefore, reducing the frictional force between the inner wall of the sheath and the stent 10, allowing a smoother retraction of the sheath 98 with less axial force.

Figure 8C:
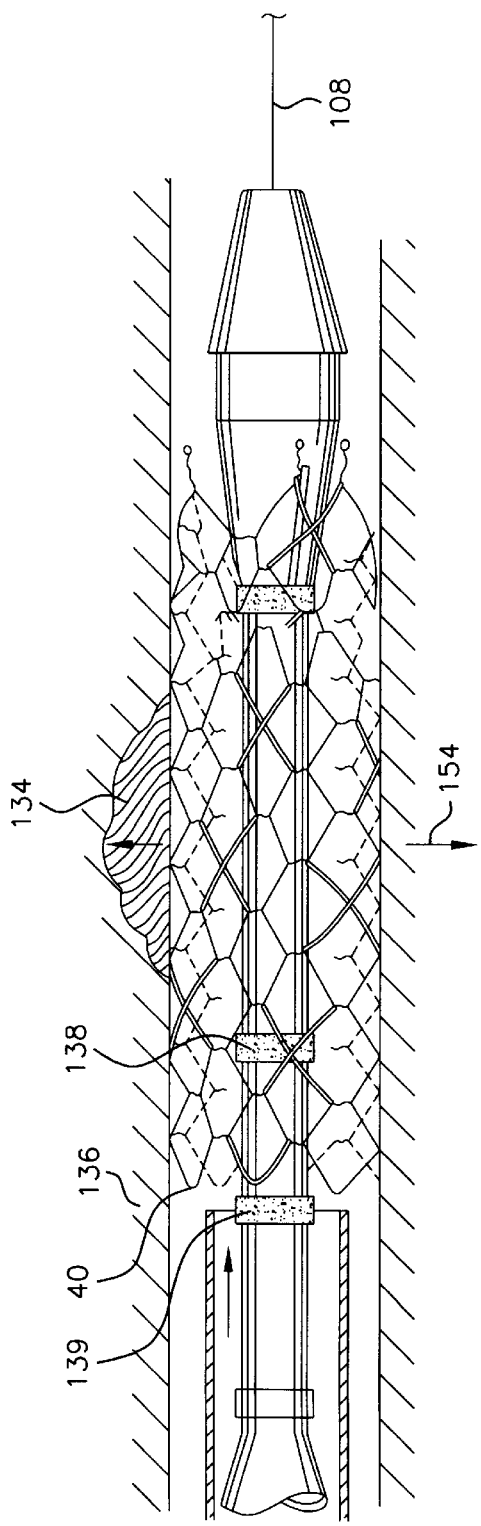

After sheath retraction continues but usually to a point less than the marker 138, the proximal end 40 of the expanding and contracting prosthesis 10 exits the sheath 98 and engages the lumen wall 136, forcing open the lumen 136 to its normal diameter and firmly anchoring the stent so that it resists axial motion, as illustrated in FIG. 8C.

Figure 8D:
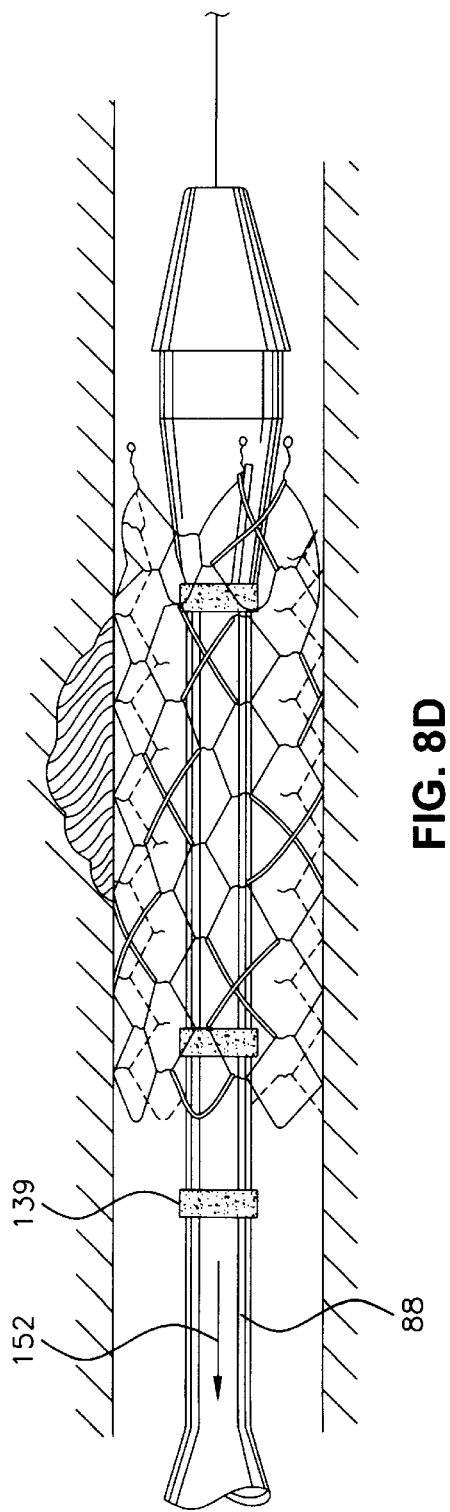

The stent is released entirely from the catheter body 88 by drawing the catheter body 88 proximally (arrow 152) as seen in FIG. 8D, which causes the end loops to be positioned at more distal positions along the members, until the radial force of the stent 10 causes the members to deflect outwardly (arrows 154).

Figure 8E:
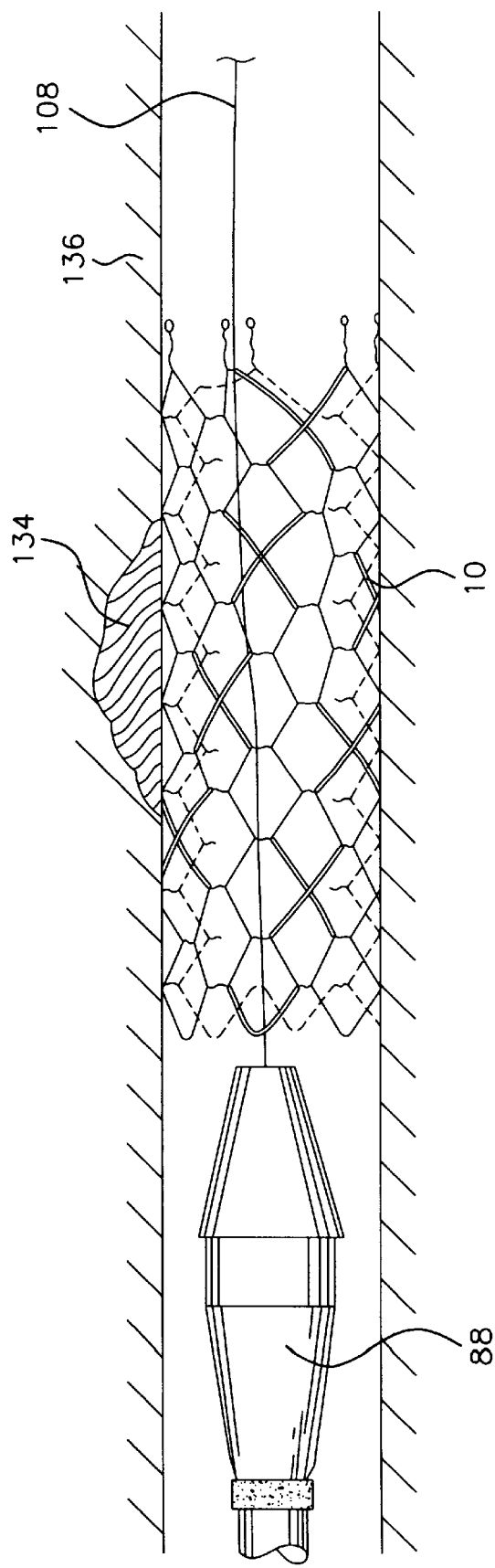

The catheter 88 is then removed from the body, leaving the prosthesis 10 properly positioned as illustrated in FIG. 8E.

Figure 9:
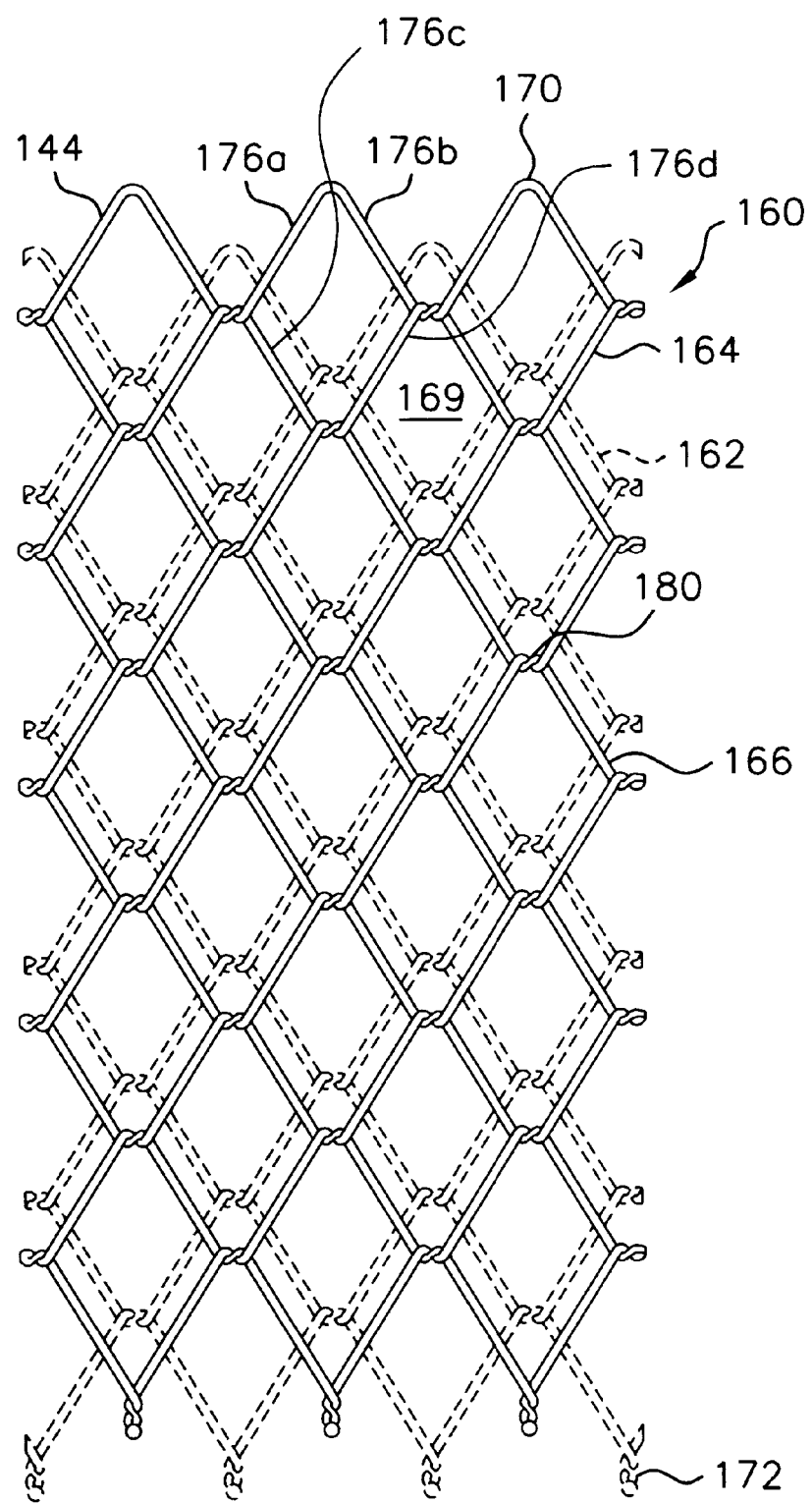
FIG. 9 is a flat layout view of a double layer stent.

An alternative embodiment of the low profile diamond stent is shown as a flat layout view in FIG. 9. The stent 160 has two separate layers 162 and 164; an inner layer 162 shown in hidden line and an outer layer 164. Each layer 162 and 164 of the stent 160 has a plurality of strands 166. In a preferred embodiment, each layer has four strands; this is in contrast to the five strands in the previous embodiment. While four and five strand embodiments are shown above, it is recognized that the number of strands and cells can vary, for example, from three to ten or higher, dependent on size, type of joint or the strands, use and other factors.

The strands are woven in a pattern of geometric cells 169 starting at the distal end 170. Each strand 166 forms a pair of legs 144 of the most distal opening on the cell 168. The inner layer 162 and the outer layer 164 are intertwined at both the distal end 170 and the proximal end 172.

The sides 176a, 176b, 176c, and 176d of each of the cells 168 are defined by a series of strand lengths 178a, 176b, 176c, and 178d. Each of the sides 176 are joined to this adjoining side at an intersection where the strands are helically wrapped about each other to form interlocking joints 180.

Similar to the embodiment shown in FIGS. 1A and 1B and in contrast to the previous embodiment, every intersection has an interlocking joint 180. Without the fifth strand 166, the stent 160 can be contracted into a smaller diameter than that of the stent 20 shown in FIGS. 1A and 1B.

In a preferred embodiment for use in a colon, both layers are formed of identical materials. Each strand is composed of nitinol and has a diameter of 0.010 inches (0.25 mm).

Still referring to FIG. 9, the two separate layers 162 and 164 in the constricted position are off-set from each other so the interlocking joints of one layer do not engage with the interlocking joints of the other layer. The off-set between layers can be created by either an off-set during manufacturing as described below, or created by the related motion of the layers as the layers are constricted. The related motion can be the result of the constraints of the strands or the material properties. One property difference can be the thickness of the strands as described in the next embodiment.

The stent can be coated with a silicon lubricant or suitable lubricant to ease the self-expanding of the stent.

Figure 10:
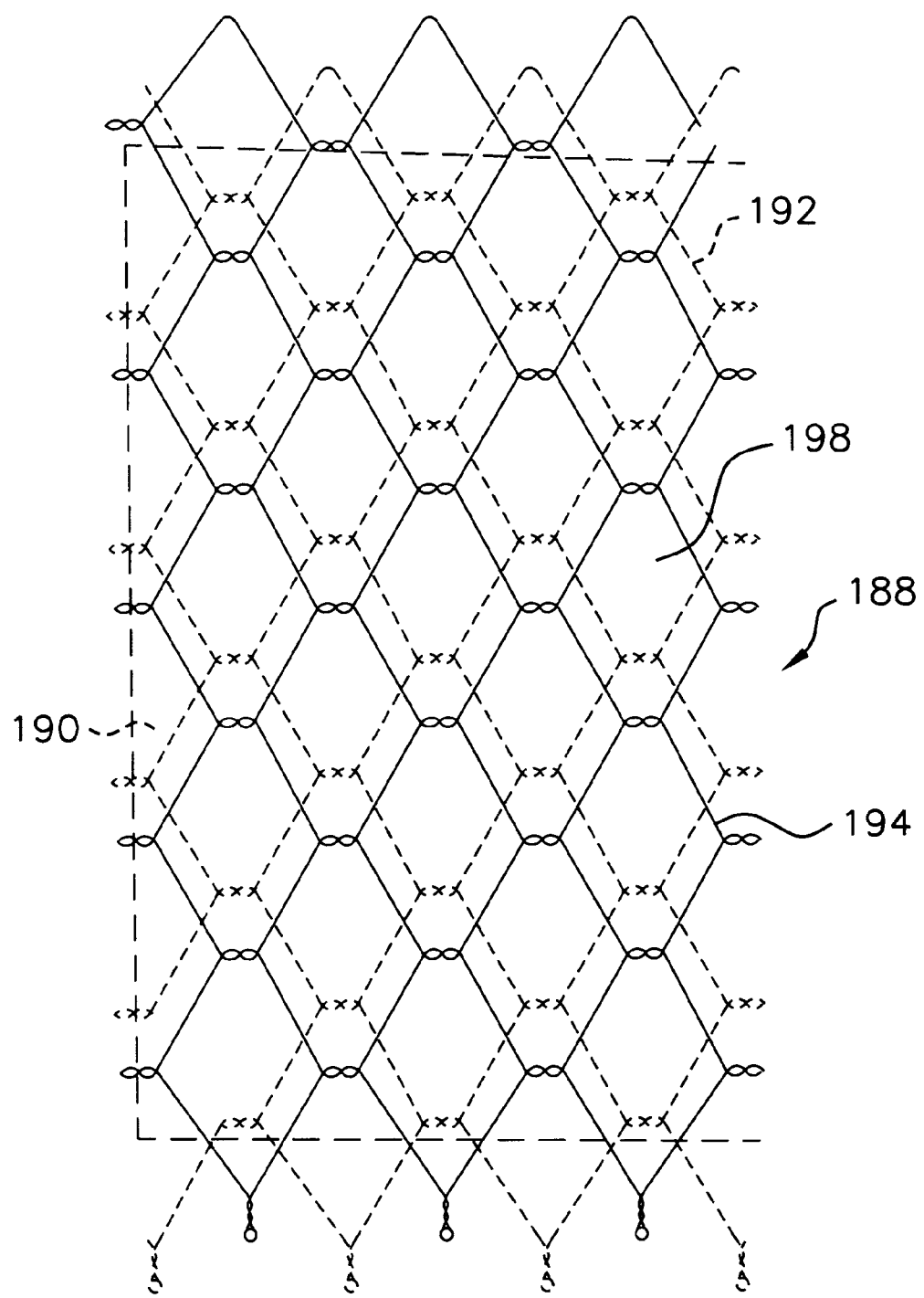
FIG. 10 is a flat layout view of an alternative embodiment of a double layer stent.

An alternative embodiment of the double layer stent 160 of FIG. 9 is shown in FIGS. 10–12. In contrast to the double layer stent 160 of FIG. 9, the double layer stent 188 has a cover layer 190 interposed between an outer layer 192 and an inner layer 194. The outer layer 192 is shown in hidden line and the cover layer 190 is shown in hidden line in FIG. 10. It is recognized that the cover layer 190 can be placed in other locations.

Similar to the previous embodiment, the inner layer 194 and the outer layer 192 are intertwined at both the aproximal end 170 and the distal end 172. The intertwining of the layers 192 and 194 retains the cover layer 190 in position.

In a preferred embodiment, each layer has four strands and are woven similar to the embodiment shown in FIG. 8 to define the geometric cells 198. The strands of the two layers are formed of two different thickness wires in a preferred embodiment. The inner layer has a thicker wire.

FIG. 11 shows the stent in an artery. The stent is moving an obstacle out of the passage. The cover prevents tumor in-growth, will seal fistulas and block aneurysms.

One technique for placing a stent into the circulation system of a patient is to enter from the brachial artery located in the arm. This point of entry can be used for insertion into the vascular system including for example, peripheral locations such as the knee which require the flexibility of the diamond stent.

A cross-sectional view of the stent 188 is shown in FIG. 12. The inner layer 194 having the thicker strands forces the cover 190 and the outer layer 192 outward. The cover 190 is in engagement with both the inner layer 194 and the outer layer 192.

In a preferred embodiment, the strands are formed of nitinol. The inner layer has strands having a diameter of 0.006 inches (0.15 mm). The strands of the outer layer have a diameter of 0.005 inches (0.13 mm). The radial expansion force of the thicker wire inner layer is transmitted to the outer layer. The radial expansion force can be altered by varying one or both layers.

In another preferred embodiment, the stent has three strands on each layer. The inner layer has a diameter of 0.008 inches (0.02 mm). The strands of the outer layer have a diameter of 0.005 (0.13 mm) inches.

The outer layer can be formed from a non self-expanding material. The outer layer can be chosen for its radiopaque characteristics. Materials that can be chosen for their radiopacity characteristics include tantalum, platinum, gold or other heavy atomic metal.

In a preferred embodiment, a cover is interposed between the layers. The cover can be made of several types of material which allow the stent to be compressed to a small diameter and also be self-expanding. A preferred material is a woven carbon fiber, a metal mesh, a polymer such as a polyurethane, or a material treated with a drug for time release. Different agents can be employed on the inside and the outside. An electrical current can be applied to tissue using the stent. Different materials for the layers can be used than the interposed cover depending on the treatment site and the desired method of treatment.

Figure 13:
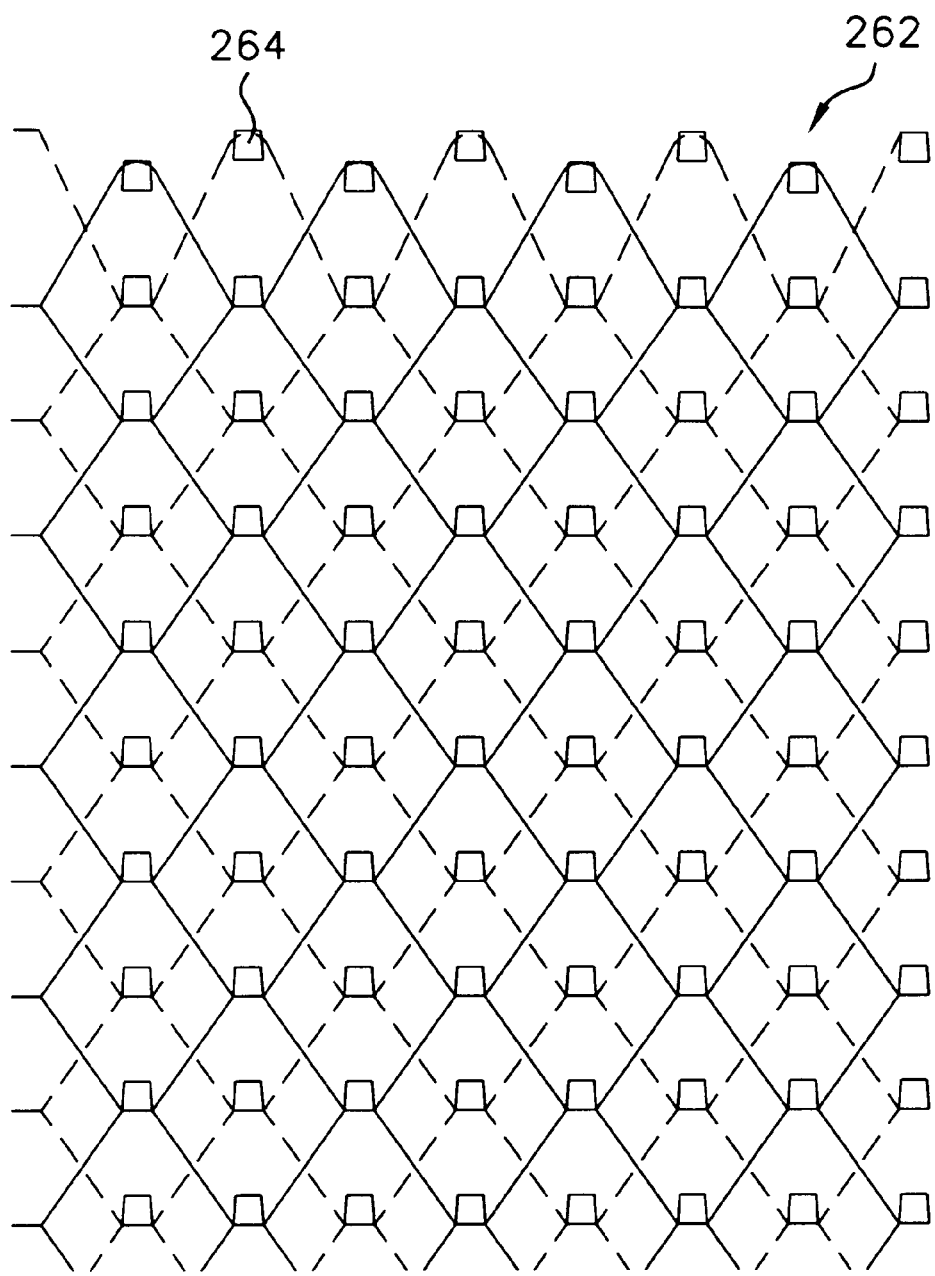
FIG. 13 illustrates a mandrel for making a stent of FIGS. 9 or 10 and 11.

In one preferred embodiment, the layers 192 and 194 are interwoven for the entire stent without an interposed cover. Referring to FIG. 13, a mandrel 262 has a plurality of anchoring pins 264. For a stent having two layers of four strands each, each row has eight (8) anchoring pins 264 at the same height. The top row, however, has the anchoring pins 264 for one strand positioned ½ millimeter higher than the other set. After the stent is woven, the distal end of each stent is pulled to the same position, therein resulting in the rest of the interlocking joints being offset.

If there is no cover between the two layers, the two layers can be interwoven from the distal end to the proximal end.

FIGS. 14A and 14B illustrate a single layer stent 210 having six strands. The stent 210 has four wrap joints 254 a pair of cross joints 256. FIGS. 14C and 14D show enlarged views of two parts of the stent shown in FIG. 14A.

In one preferred embodiment, the stent 210 has a diameter of 14 millimeters in the expanded state. The stent has foreshortening in the range of 12 to 18 percent. With the strands having a diameter of 0.006 inches (0.15 mm), the stent with only four wrap joints 254 per row can compress to fit within a 7 French system.

Figure 15A:
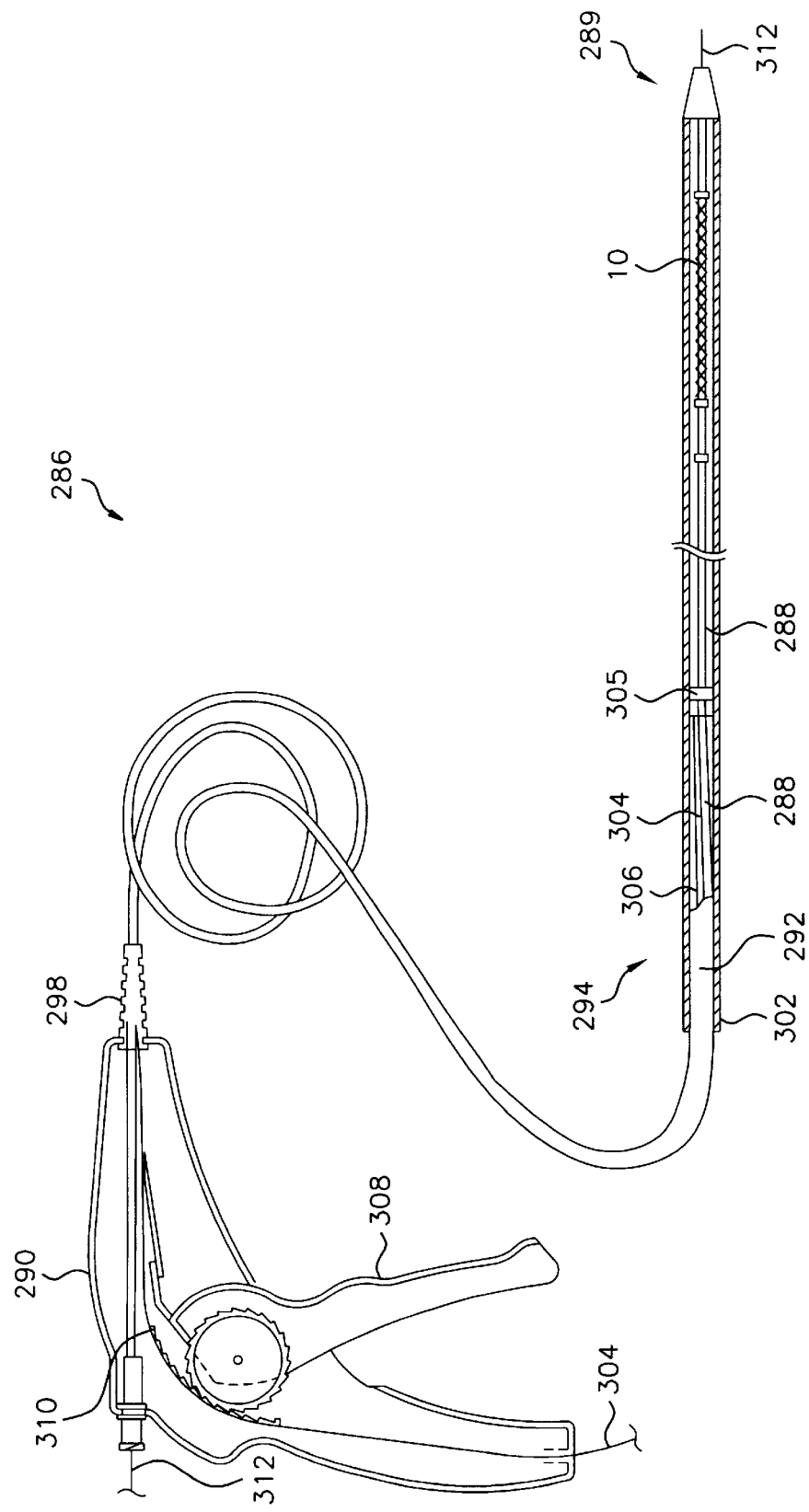
FIG. 15A is a side view with portions broken away of an alternative embodiment of an "over-the-wire" delivery system.

An alternative delivery system 286 is illustrated in FIG. 15A. The stent 10 is positioned over an inner shaft 288, which is a braided tube, at a distal end 289 of the delivery system 286. The inner shaft 288 extends to a proximal handle 290. The delivery system 286 has an outer shaft 292 which extends from the proximal handle 290 to a point 294, which is proximal the distal end 289. The inner shaft 288 extends through a lumen 296 of the outer shaft 292 from the proximal handle 290 and projects out at the distal end of the outer shaft 292. The inner shaft 288 secured to a luer fitting 298 housed in the proximal handle 290, also referred to as an actuator housing or gun portion, of the delivery system 286. The inner shaft 288 is free-floating with the lumen 296.

An outer sheath 300 overlies the inner shaft 288 and the outer shaft 292 from the distal end 289 of the inner shaft to a point 302 of the delivery system 286. The outer sheath 300 is movable relative to the inner shaft 288 and the outer shaft 292 and is pulled from the distal end 289 of the inner shaft 288 using a pull wire 304 which extends in a second lumen 306 of the outer shaft 292. The distal end of the second lumen 306 is proximal to the distal end of the lumen 296. The outer sheath 300 and the pull wire 304 are pulled using an actuator 308 of the delivery system 286. The pull wire 304 is attached to a toothed strip 310 that engages the actuator 308. A guidewire 312 extends through the inner shaft 288 from the proximal handle 290 to the distal end 289.

In a preferred embodiment, the outer shaft 292 ends between 1.8 and 20.0 centimeters before the distal end 289. The outer sheath 300 extends from the distal end 289, in the range of 1 to 50 centimeters towards the proximal handle.

Referring to FIG. 15B, an enlarged view of the delivery system where the inner shaft 288 extending from the outer shaft 292 is shown in FIG. 15A. The inner shaft 288 is shown projecting from the lumen 296 of the outer shaft 292. The outer shaft 292 narrows at its distal end to minimize large discontinuities of material. The pull wire 304 is above the outer shaft 292 and can extend around the inner shaft 288. The pull wire 304 is carried by the second lumen 306 of the outer shaft 292 to a point just proximal to this location. The pull wire 304 extends down and is connected to the sheath 300 by a pull ring 305. The pull ring 305 in a preferred embodiment is sintered to the outer sheath 300. The inner shaft 288 is free to move within the lumen 296 of the outer shaft 292 at this point.

Figure 15C:
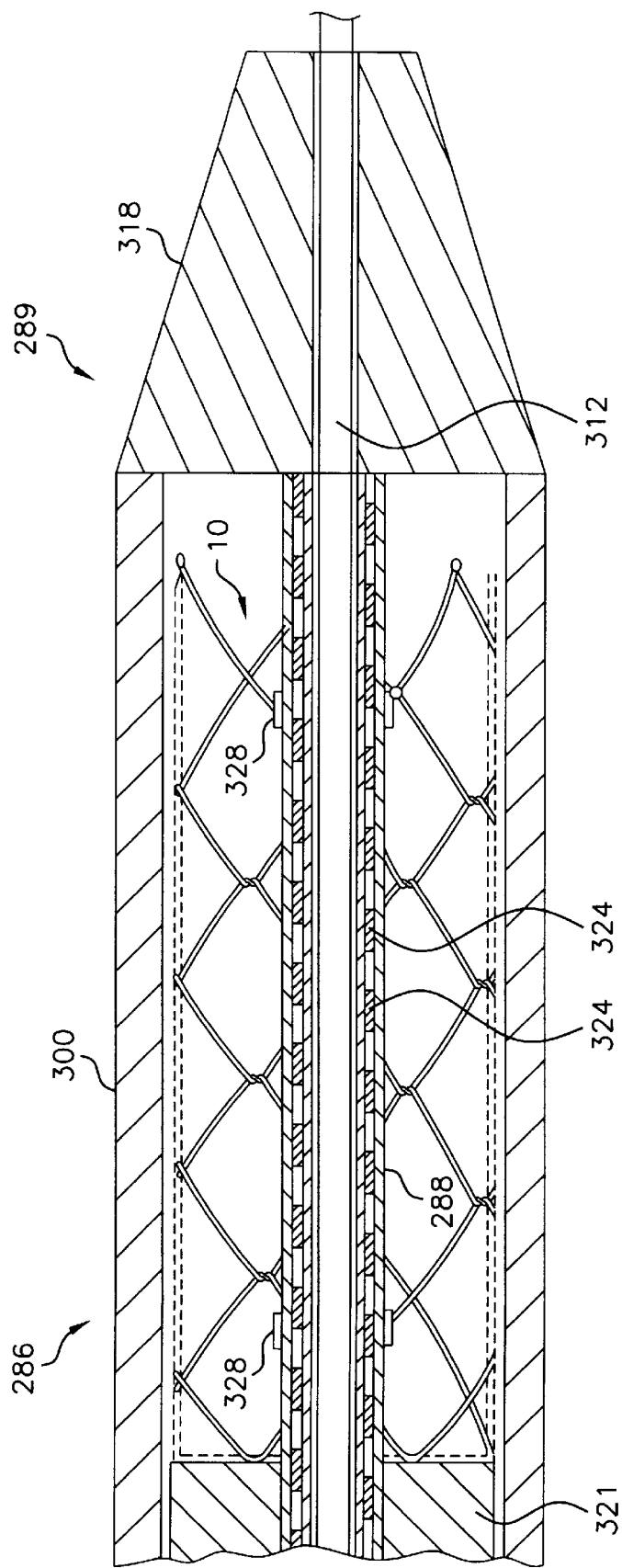
FIG. 15C is an enlarged view of the distal end of an "over-the-wire" delivery system.

The distal end 289 of the delivery system 286 is shown enlarged in FIG. 15C. At the end of the inner shaft 288 there is located a distal tip 318. In a preferred embodiment, the tip is formed of a polymer which has been molded onto the inner shaft 288. Overlying the inner shaft 288 is the stent 10. The stent 10 is positioned by a reference locator/stop 321. The outer sheath 300 overlies the inner shaft 288 and the stent 10, and engages the distal tip 318. A pair of radiopaque markers 328 are shown encircling the inner shaft 288.

Figure 16B:
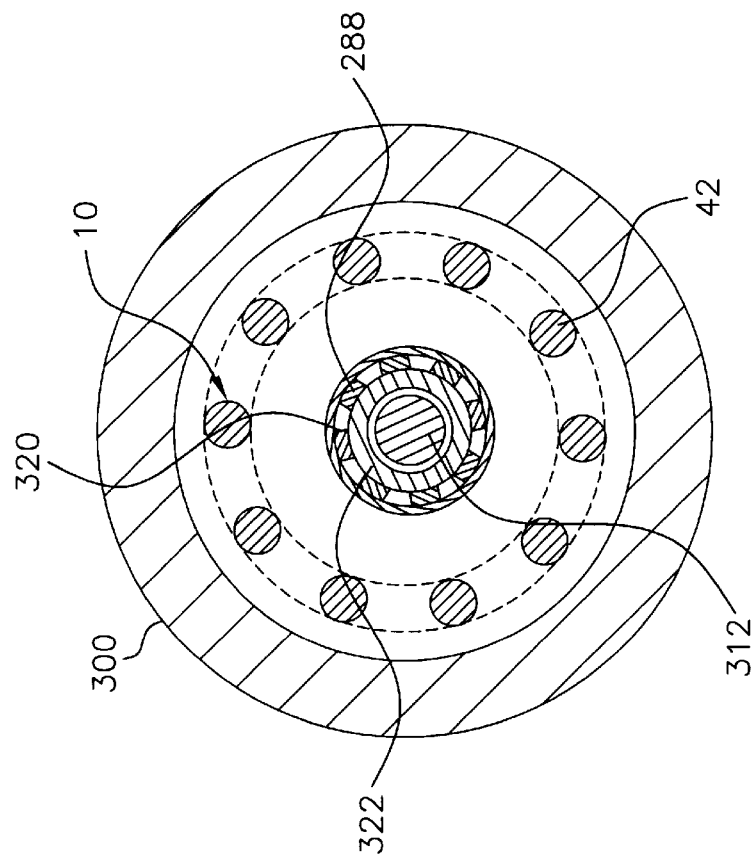
FIG. 16B is a sectional view taken along the line 16B—16B of FIG. 15C.
Figure 16A:
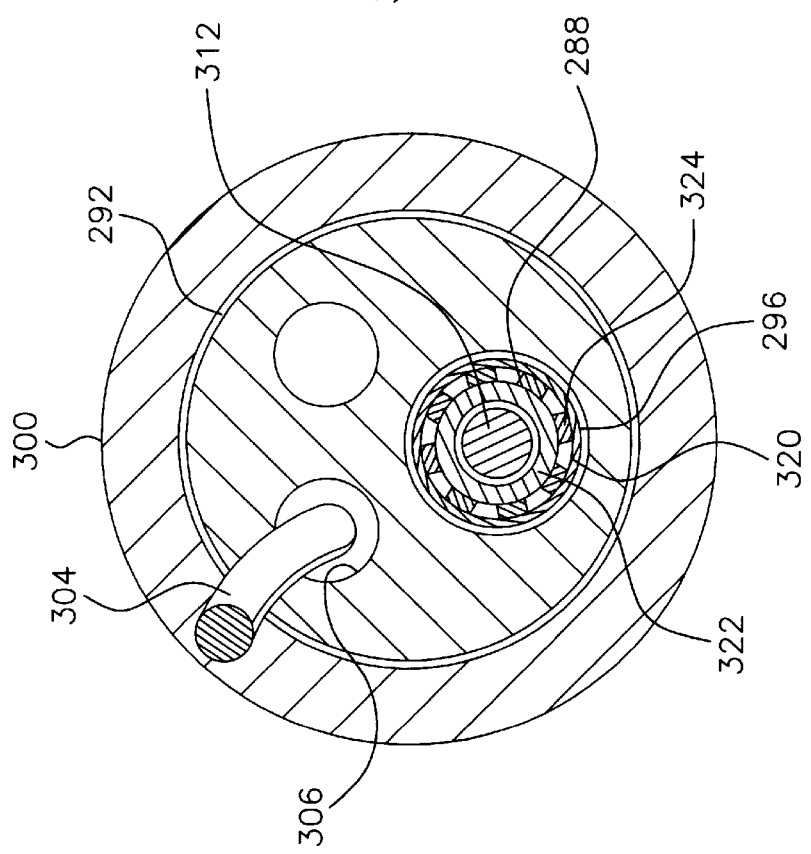
FIG. 16A is a sectional view taken along the line 16A—16A of FIG. 15B.

Referring to FIG. 16A, a sectional view of the inner shaft 288 projecting from the lumen 296 of the outer shaft 292 is shown. The outer sheath 300 can be formed of various biocompatible polymers such as a polyamide with a center core of liquid crystal polymer (LCP). It is recognized that the outer sheath 300 can be formed of other compositions as discussed above and below in alternative embodiments. In a preferred embodiment, the outer sheath 300 has an outside diameter of 4–7 French. The wall thickness is typically 0.003 to 0.005 inches (0.076 mm to 0.13 mm).

The outer shaft 292 has an outer diameter of 0.066 inches (1.7 mm), which allows the proximal end of the outer shaft 292 to fit within the outer sheath 300. The outer shaft 292 in a preferred embodiment is made of polyamide or nylon, but can alternatively be made of other biocompatible polymers such as polyester, polyurethane, PVC or polypropylene. The lumen 296 of the outer shaft 292 has a diameter of 0.035 to 0.037 inches (0.89 to 0.94 mm), for example, and receives the inner shaft 288. The outer shaft 292 in a preferred embodiment has a plurality of other lumens including the second lumen 306 which the pull wire 304 extends through. In a preferred embodiment, the second lumen 306 has a diameter of slightly larger than the pull wire 304. The pull wire 304 is typically a single stainless steel wire having a diameter of 0.012 inches (0.30 mm). However, the pull wire 304 can consist of a plurality of wires and can be formed of a different material.

The inner shaft 288 is formed of a reinforced layer encased by an outer layer and an inner layer. In a preferred embodiment, the inner shaft 288 has as a center reinforcement layer comprising of a tubular woven steel braid 320. The reinforcement layer is encased by the inner and outer layer of polyimide 322. The tubular woven steel braid is formed of flat strands 324 having a thickness of 0.0015 to 0.003 inches (0.038 mm to 0.076 mm) and a width of 0.001 to 0.005 inches (0.025 to 0.13 mm) in a preferred embodiment. The inner diameter of the tubular woven steel braid is 0.015 to 0.038 inches (0.38 mm to 0.97 mm). The tubular steel braid is encased in the polyimide such that in a preferred embodiment the outer diameter of the inner shaft 288 0.021 to 0.041 inches (0.53 to 1.0 mm). The thickness of the wall of the inner shaft is typically between 0.003 to 0.008 inches.

Within the inner shaft 288 a guidewire 312 may extend as seen in FIG. 16A. The guidewire 312 in a preferred embodiment is formed of stainless steel. The guidewire 312 in a preferred embodiment has a diameter in the range of 0.014 to 0.037 inches (0.36 to 0.94 mm) and in a preferred embodiment 0.035 inches (0.89 mm).

Referring to FIG. 16B, a sectional view of the distal end of the delivery system is shown. The sheath 300 is overlying the inner shaft 288 with the stent 10 being interposed. The pull wire 304 seen in FIG. 16A is secured to the sheath at a position proximal to that shown in FIG. 16B.

The delivery system 286 can be used in numerous ways. One such way is by placing the delivery system's outer shaft 292 and inner shaft 288 through an endoscope 70 such as shown in FIGS. 5A and 5B. Alternatively, a percutaneous procedure can be used. In both procedures, the guidewire extending through the inner shaft 288 is extended beyond the inner shaft 288 and used to define the path. The inner shaft 288 is to be pushed a short distance along the guidewire. The guidewire and inner shaft 288 are moved until the distal tip is in position.

The inner shaft 288 has sufficient strength that it is able to follow the guide wire and resist kinking. Overlying the inner shaft 288 is the outer sheath 300 which gains its structural strength by engaging and forming a continuous structure with the distal tip 318 of the inner shaft. The sheath 300 is pulled in the proximal direction to expose the stent 10 as explained above and therefore does not have to slide over the distal tip 318 of the inner shaft 288.

The stent 10 is located between the outer sheath 300 and the inner shaft 288. The inner shaft 288 is secured only at the luer fitting 298 housing the proximal handle 290 of the delivery system 286. The inner shaft 288 floats freely and is not otherwise secured within the lumen 296 of the outer shaft 292.

When the distal tip is in the proper position in the artery, vessel or other desired location, the outer sheath 300 is pulled proximally by using the handle on the proximal handle 290 which engages an actuator 308 that moves the tooth strip 310. The tooth strip 310 is connected to the pull wire 304 which extends through a lumen in the outer outer shaft to a point beyond the proximal end of the outer sheath and the pull wire extends from that point to the pull ring. With the outer sheath moved proximally, the stent 10 is able to self expand into proper position.

Figure 17A:
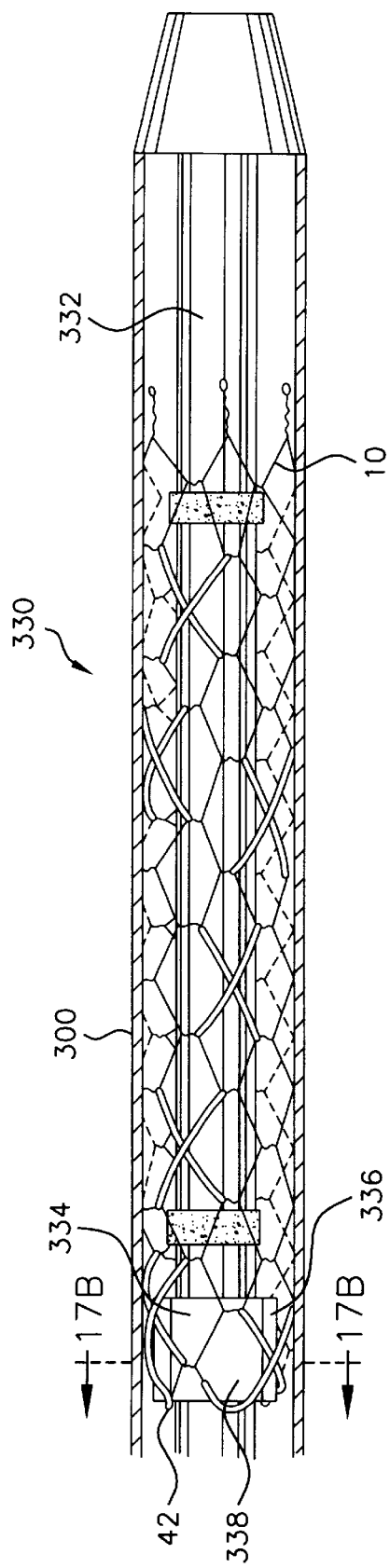
FIG. 17A is a side view of a portion of the catheter showing a locking ring.
Figure 17B:
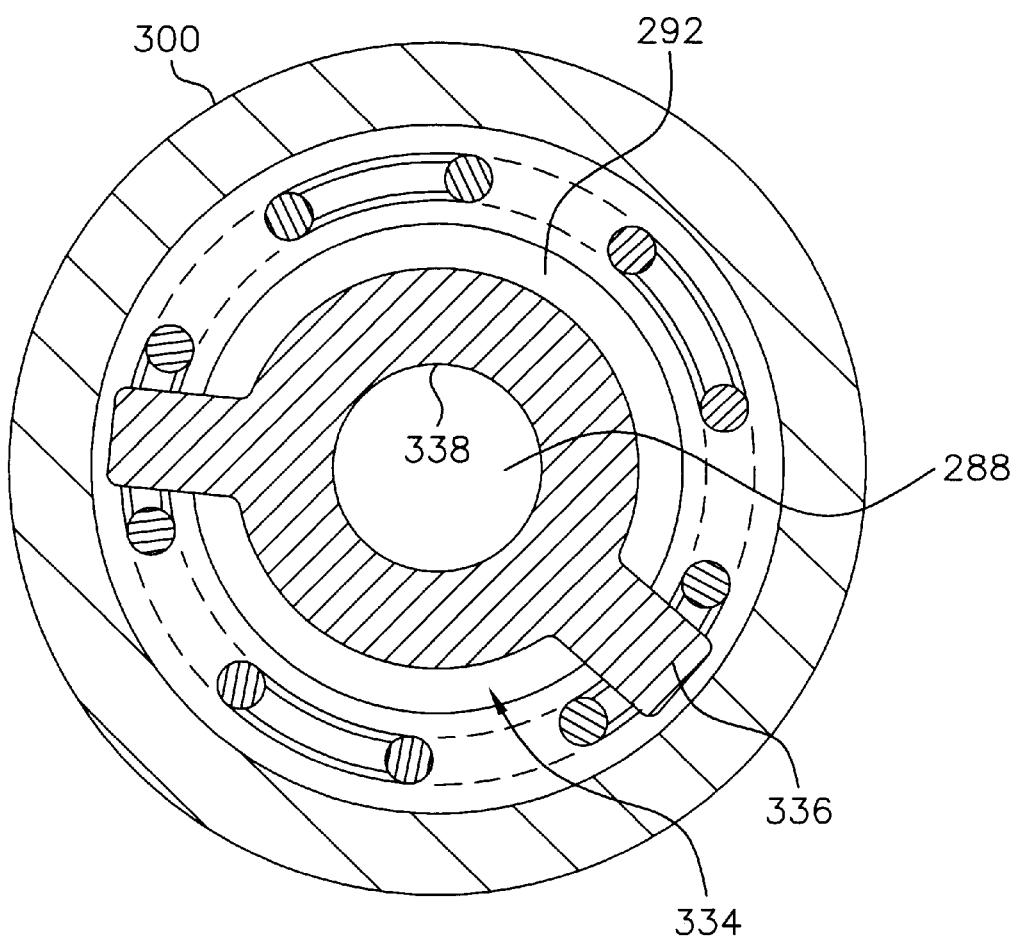
FIG. 17B is a sectional view taken along line 17B—17B of FIG. 17A showing the interaction of the locking ring with the stent.

Referring to FIGS. 17A and 17B, an alternative embodiment of a delivery system 330 is shown. The delivery system inner shaft 332 which is encircled by an inner ring 338 of a mounting ring 334. The mounting ring 334 has at least one radial member or ridge 336, which projects radially out from the inner ring 338 towards the outer sheath 300. In a preferred embodiment, the ring 334 has a pair of ridges 336 which project radially outward in opposite directions along a common axis, or in other words, at an angular separation of 180 degrees. Additional ridges 336 that can be evenly spaced around the circumference of the ring 334 to evenly distribute the load force on the stent and can extend longitudinally between 1 and 8 mm such that the proximal loops at one end of the stent grasp the ridges during mounting. The stent is then held in place by the outer sheath during delivery and release. For example, three members 336 are spaced 120 degrees apart round 334.

Cells of the stent 10 are placed around the protrusions 336. With the strands 42 of the stent 10 encircling the tabs 336, the stent 10 can compress while still being retained. Placement of the members at the proximal end of the stent 10 affords maximum extension and compression of the stent to within the needed diameters.

An alternative method uses a solid mounting ring where the stent is held with a friction fit between the outer sheath and the ring to retain the stent in position in the delivery system. The solid ring with the friction fit is further described in U.S. Pat. No. 5,702,418 which issued on Dec. 30, 1997, the entire contents of which is incorporated herewith by reference.

Figure 17C:
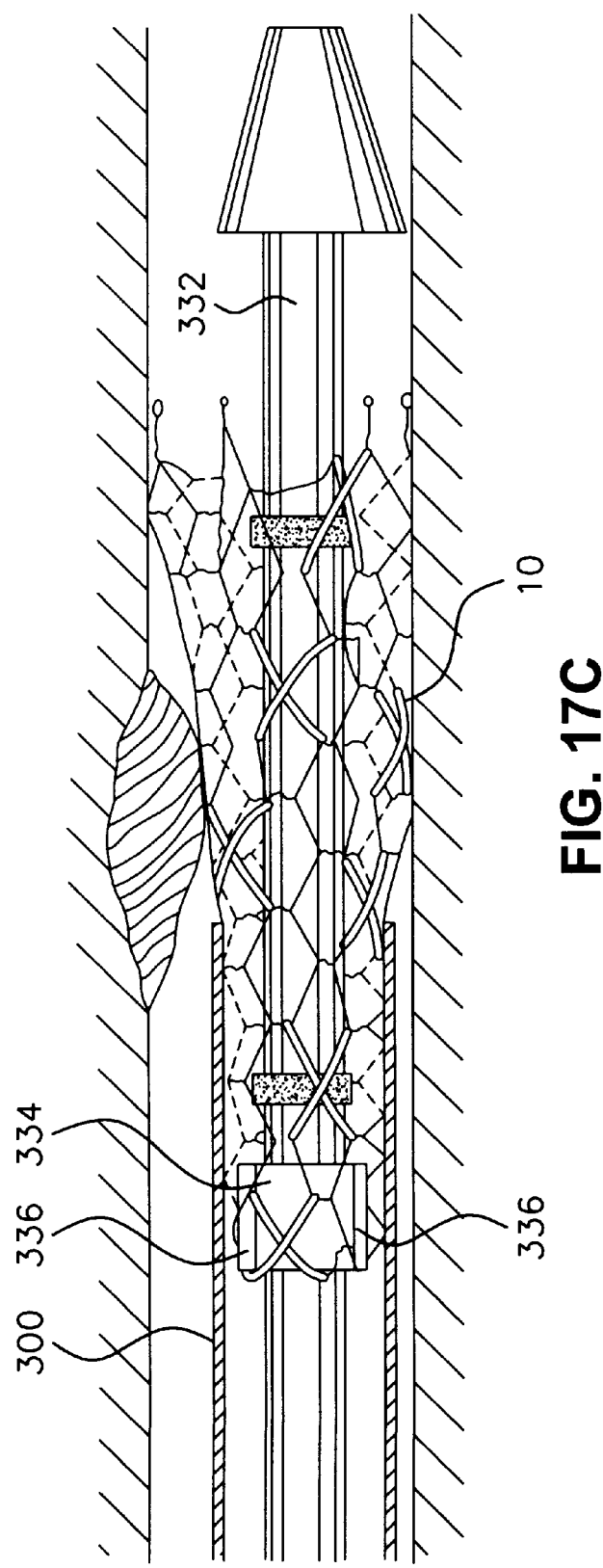
FIG. 17C is an illustration of a partially deployed stent with a locking ring.

Alternatively, as seen in FIG. 17C, the tabs or ridges 336 of the ring 334 retain the stent 10 as the stent 10 is deployed. If it is determined prior to the stent 10 being totally deployed that the stent is not in proper position, the stent can be retracted back into the delivery system.

In a preferred embodiment, the inner ring 334 has an outer diameter of 0.05 inches (1.3 mm). The tabs 336 project such that the distance from the radial end of one tab 336 to the radial end of a tab on the other side of 0.07 inches. The tabs have a width of 0.01 inches. The ring 334 can have a length of 0.06 inches.

Figure 18:
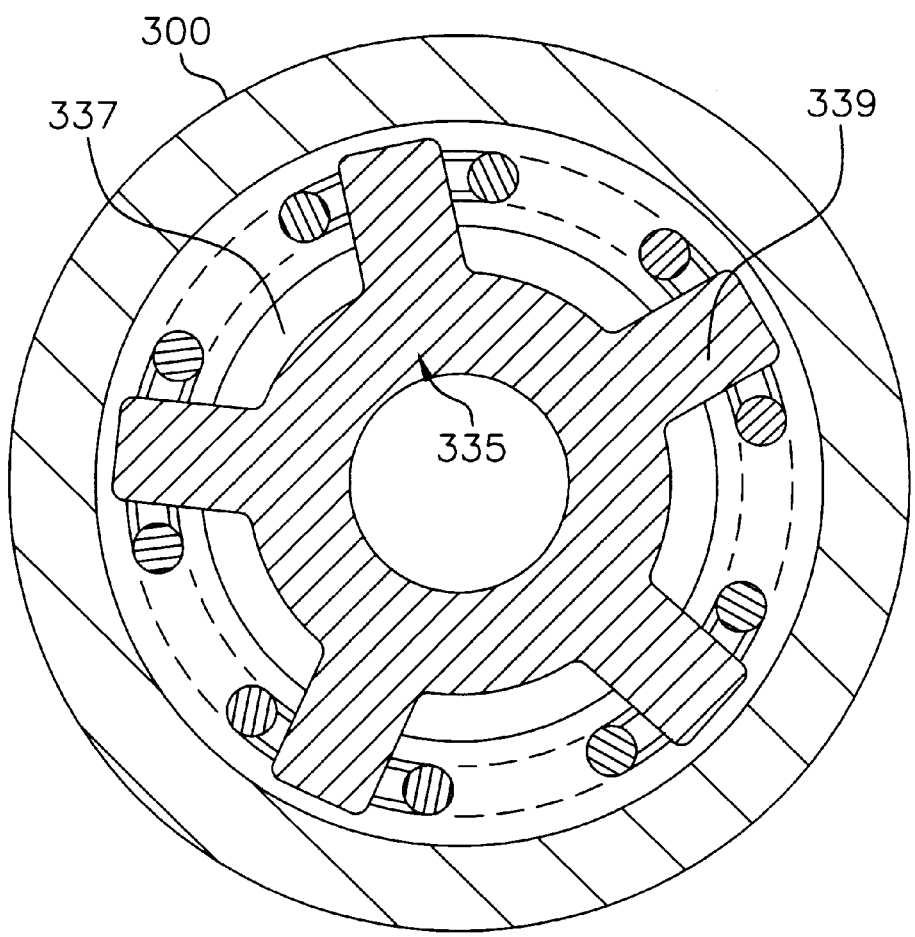
FIG. 18 is a sectional view showing an alternative lock ring with the stent.

FIG. 18 shows an alternative mounting ring 335. The ring 335 is a solid ring with sections removed to define a plurality of grooves 337. The grooves 337 receive the strands of the stent 10, with the projections or ridges 339 located in the cells of the stent 10.

Figure 19A:
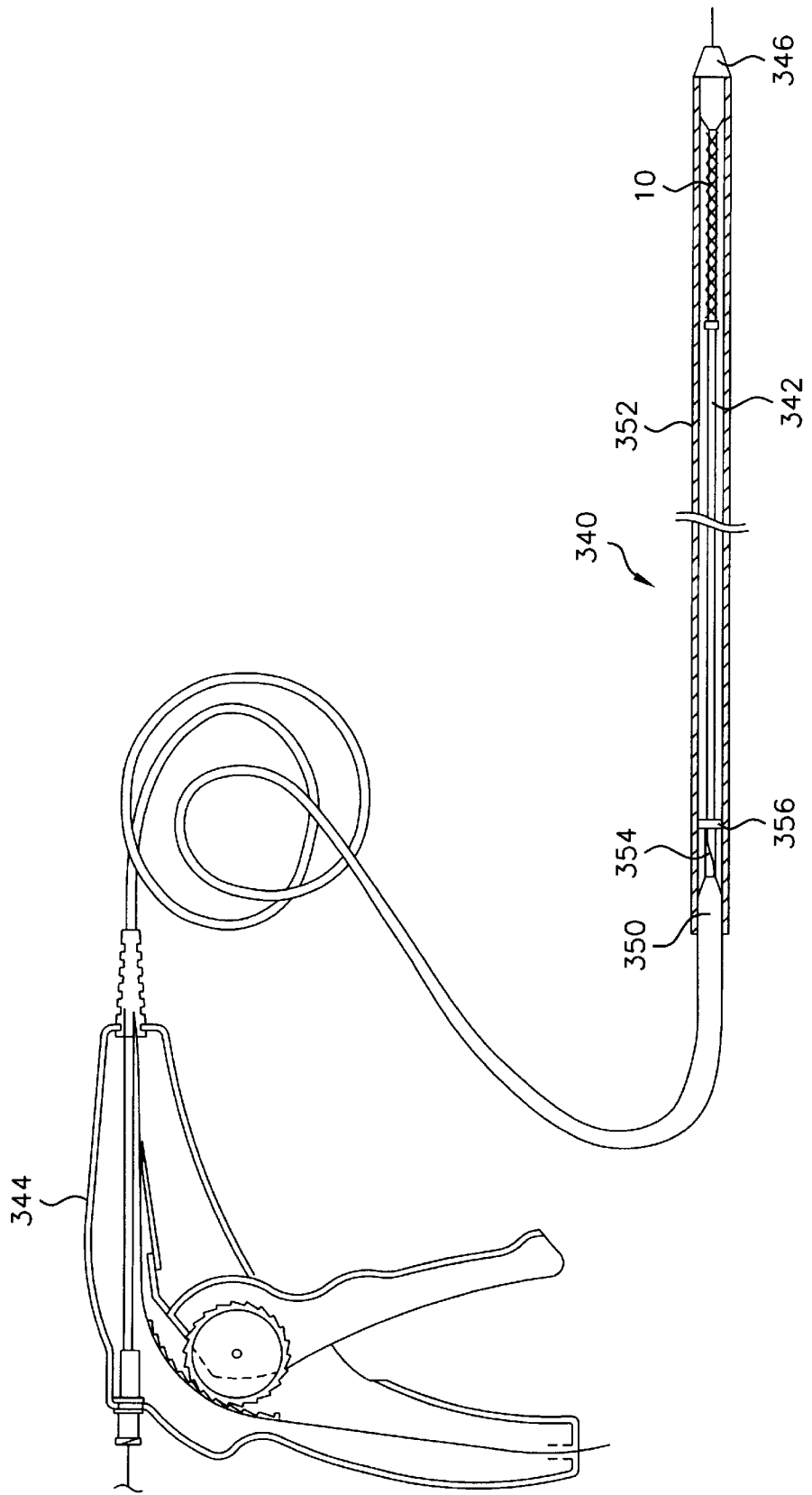
FIG. 19A is a side view, with portions broken away, of an alternative embodiment of an "over-the-wire" delivery system.

Similar to the previous "over-the-wire" delivery system shown, an "over-the-wire" delivery system 340 shown in FIG. 19A has an inner shaft 342 extending from a proximal handle 344 to a distal tip end 346. The inner shaft 342 extends through an outer shaft 350 at the proximal end. An outer sheath 352 is located at the distal end of the "over-the-wire" delivery system 340, overlying the exposed inner shaft 342 and a portion of the outer shaft 350. The outer sheath 352 is moved toward the handle using a pull wire 354 and a pull ring 356. The pull wire 354 extends through a lumen 348 of the outer shaft 350 from the proximal handle 344 to a point just proximal to where the inner shaft 342 extends from the outer shaft 350.

Figure 19B:
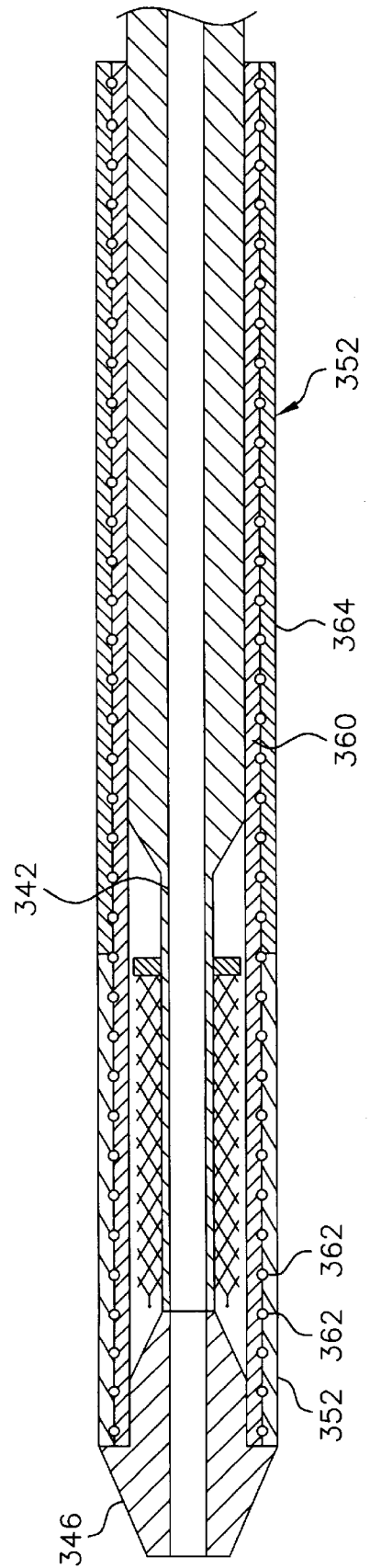
FIG. 19B is an enlarged view of the distal end of the "over-the-wire" delivery system of 19A.

Referring to FIG. 19B, the outer sheath 352 is formed of several layers of material. An inner layer 360 can be formed of a nylon 12 which extends the entire length of the outer sheath 352. Overlying the inner layer 360 is a braid 362 of either a metallic or fiberglass such as a stainless steel braid. The outer sheath 352 has an outer layer 364 formed of nylon 12 extending from the proximal end to a position proximal and adjacent to the distal end 346. The last portion of the outer layer 364 is formed of another material which is less stiff, or softer, such as a PEBAX.

In a preferred embodiment, the last portion of the outer sheath 352 which has the less stiff or softer material on the outer layer 364, extends 36 centimeter (+/−one cm) and the entire length of the outer sheath is approximately 200 cm. In a preferred embodiment, the outer diameter of the sheath is 0.920 inches (+/−0.001 inches, or about 23.4 millimeters) with the wall thickness being 0.0070 inches (+/−0.0005 inches) (0.1778 millimeter +/−0.0127 millimeter). The braid 362 is formed of a stainless steel having a diameter of 0.0015 inches (0.038 millimeter).

It is noted that the delivery systems shown can be used in various locations such as non-vascular systems and vascular systems. In the embodiment shown above, one of the application is endoscopic delivery in the gastric system which requires that the delivery system be capable of taking a 90 degree bend. The inner shaft, sometimes referred to as the catheter, has an outer diameter that approximates the inner diameter of the outer sheath, for a segment near the distal end, just proximal to where the stent is positioned, as seen in FIG. 19B. This is in contrast to the embodiment shown in FIG. 16B.

Figure 20A:
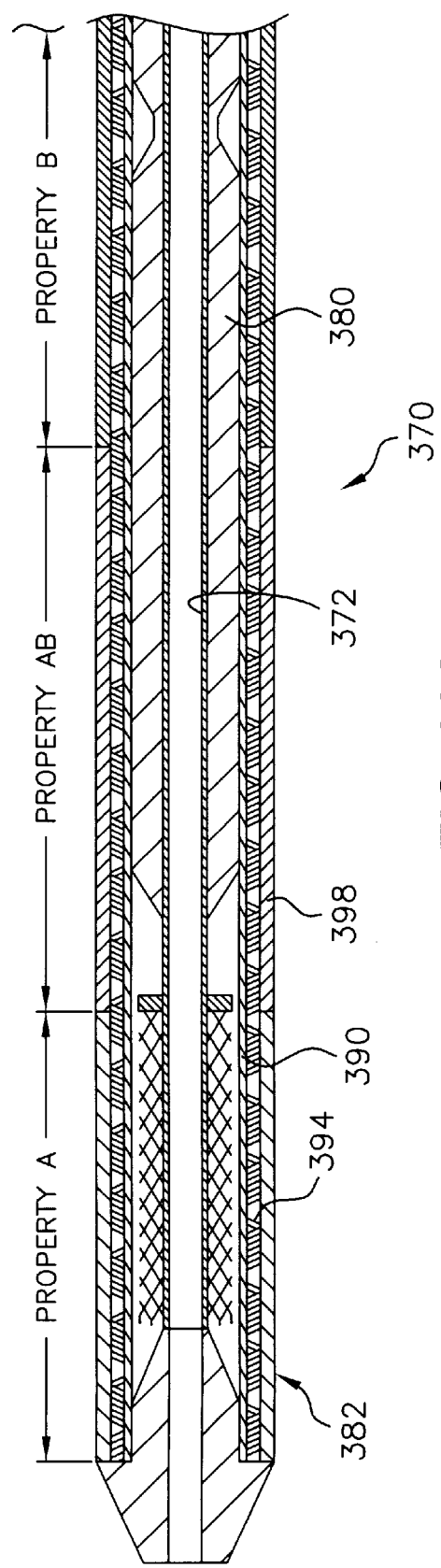
FIG. 20A is an enlarged view of the distal end of an alternative embodiment of an "over-the-wire" delivery system.

An alternative embodiment of an "over-the-wire" delivery system 370 is shown in FIGS. 20A and 20B. The delivery system 370 has an inner shaft 372 seen from the proximal handle 374 to a distal tip end 376. The inner shaft 372 extends through an outer shaft 380 at the proximal end. An outer sheath 382 is located at the distal end of the "over-the-wire" delivery system 370.

This embodiment has the same elements as the previous embodiment. The outer sheath 382 has variable properties as explained below. As indicated above, it is recognized that the path the delivery system takes is almost never straight and usually has many bends between the insertion point into the body and the stricture or stent delivery site. In order to reach the delivery site, the delivery system including the outer sheath 382 must be flexible enough to negotiate the bends, but have sufficient strength and stiffness.

The outer sheath 382 is formed of a plurality of layers. An inner layer 390 is formed of a fluorinated polymer such as PTFE or FEP, or polymer such as HDPE. A second layer 392 (shown in FIG. 20B) encases the first layer and consists of a polyurethane such as those sold underneath the name TECOFLEX™ or PLEXAR™. A third layer 394 consists of a polymer braiding, such as LCP fiber (Vectran), or a metal braided coil. In a preferred embodiment, the braiding is flat. However, it is recognized that a round braiding may also be used. A fourth layer 398, an outer layer, of the outer sheath 382 material properties vary as it goes from the proximal end to the distal end.

In a preferred embodiment, the properties of this fourth layer 398 are divided into two materials and a combination of these materials in the transition. For example, the first portion is a material/blend chosen for higher density, crush strength, relative high durometer and stiffness such as a polyamide sold under the trade name Cristamid or HDPE. The material at the distal end being selected for a higher flexibility, crease resistance, such as a polyamide with lower durometer or Pebax material (polyamid elastomer). In a transition area the material starts as a high 100 percent of the A property and transitions to 100 percent of the B property. This transition area in a preferred embodiment is less than one centimeter; however, the transition area can be up to lengths of 25 centimeters.

FIG. 20B is an enlarged view of the outer sheath 382 extending from the distal end to the proximal end, with portions broken away. The inner shaft 372 and stent 10 have been removed from FIG. 20B to allow greater visibility of the metal braided coil. The metal braid is formed of a flat wire having a width of between 0.001 inches (0.025 mm) and 0.005 inches (0.13 mm) and a thickness of 0.001 inches (0.025 mm). For the LCP fiber braid, the width is 0.003 inches (0.076 mm) and a thickness of 0.0007 inches (0.018 mm) diameter. The stiff materials could also be polyester (PET), LCP (liquid crystal polymer), PEEK, PBT, etc. and the soft material could be polyester elastomer, Arnitel or Hytrel. Weave patterns can be one-over-one or two-over-two. The pick density could be 20 pick/in or 120 pick/in, or vary in between While the tailoring of the properties of the outer sheath 382 can be done for main purpose of ensuring sufficient strength and flexibility. For example, it is desirable that the distal end have sufficient flexibility and still have sufficient hoop or radial strength to prevent the self expanding stent from rupturing the sheath. The tailoring of the properties can allow the overall wall thickness and therefore the outer diameter to be reduced.

The dimensions given are for a preferred embodiment. It is recognized that the dimension and properties will vary depending on the intended use of the delivery system. For example, the overall outer diameter of the composite outer sheath 382 could vary from under 3 French (e.g. for a Radius™ (Coronary) delivery system) to 20 French or larger (e.g. for a colonic or aortic delivery system). The wall thickness can vary from as thin as 0.003 inches for example, for coronary use, to as thick as 0.050 inches, for example, for colonic or aortic use. In the preferred embodiment described here, the normal thickness is 0.005 inches. It is recognized that in addition to a seamless transition where the property of the outer layer, the fourth layer 398, varies through a transition portion, the sections can vary more abruptly such as with lap joints.

Referring to FIG. 20C, a sectional view of the distal end of the outer sheath is seen. The inner layer 390 has an inner diameter of for example between 0.078 inches to 0.081 inches (1.98 to 2.06 mm) for a 7 French delivery system. The outer diameter of the inner layer is between 0.082 to 0.083 inches (2.1 mm). The second layer 392, which encases the first layer 390, has an outer diameter of 0.084 inches (2.1 mm). The third layer with a fiber braid of 0.0007 inches has an outer diameter of 0.0868 inches (2.2 mm). The open area of the third layer is filled with material from both the fourth layer and the second layer. The fourth layer has an inner diameter of between 0.087 inches and 0.088 inches (2.21 mm to 2.23 mm) and an outer diameter of between 0.091 inches and 0.092 inches (2.31 mm and 2.34 mm).

The third layer which consists of LCP fiber braid or metal braided coil could have variable pick density from proximal end to distal end. At the proximal end, the pick density is 20 pick/in for additional stiffness and tensile strength, and at the distal end, the pick density is 120 pick/in for additional flexibility and radial strength to restrain the stent in the delivery system. The transition length can be abrupt or gradual (1 cm to 25 cm).

Figure 21:
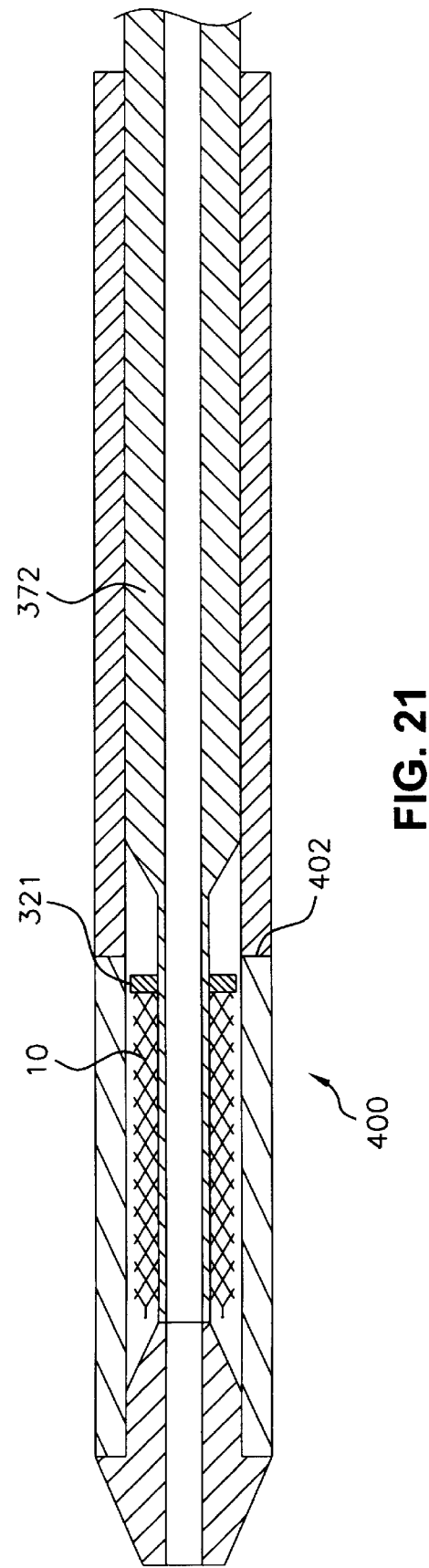
FIG. 21 is an enlarged view of an alternative embodiment of an "over-the-wire" delivery system.

An alternative embodiment of an "over-the-wire" delivery system 400 is shown in FIG. 21. The delivery system 400 has an outer sheath 402 formed of a plurality of layers. The outer layer as its material properties vary as it goes from the proximal end to the distal end.

In a preferred embodiment, the properties are divided into two materials and a combination of these materials in the transition area. For example, the first portion is a material/blend chosen for higher stiffness, crush-strength and having relative high durometer. The material at the distal end being selected for a higher flexibility, crease resistance and with a lower durometer.

In a preferred embodiment, the outer sheath does not have a layer containing a polymer or metal braided coil.

Figure 22A:
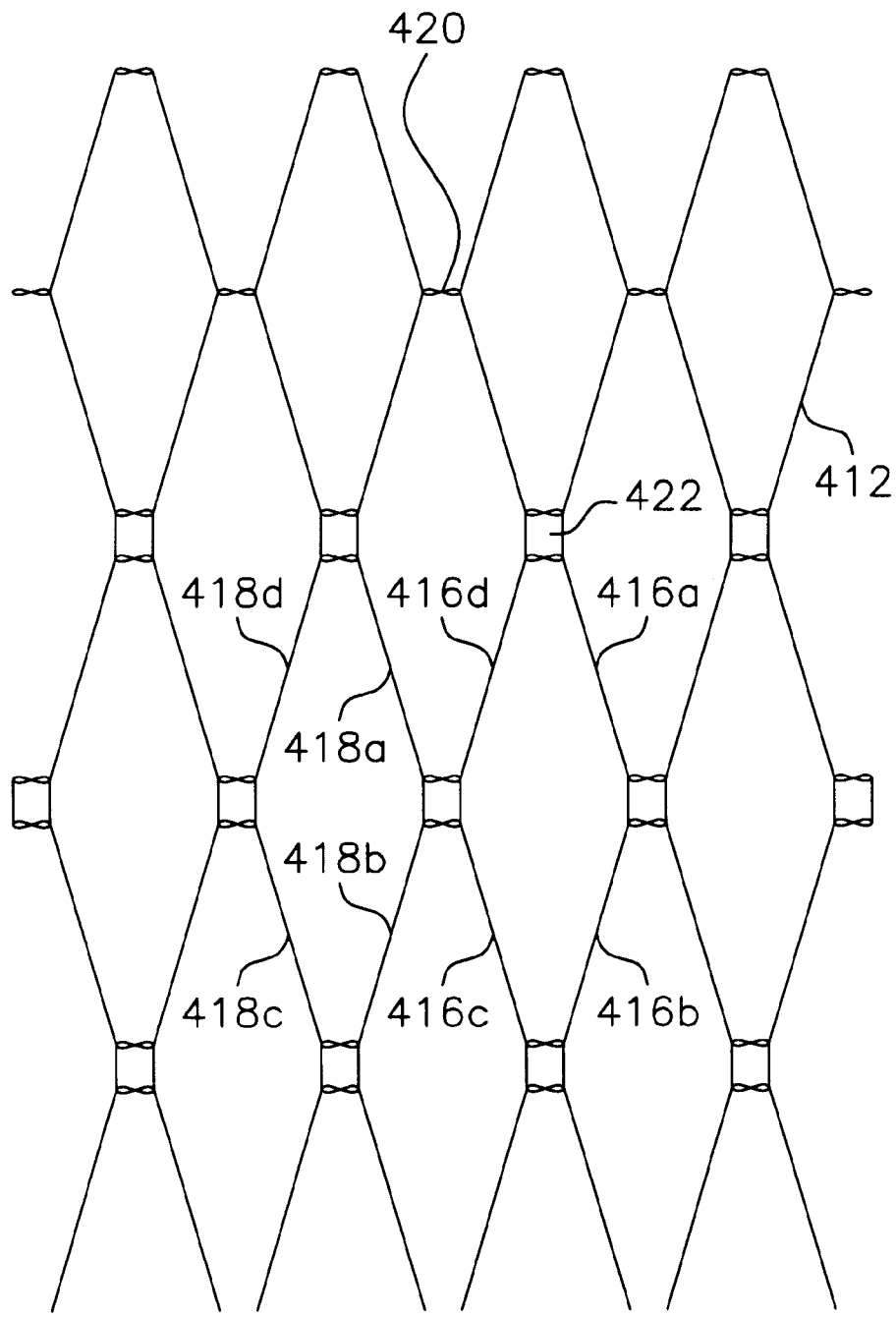
FIG. 22A is a flat layout view along the longitudinal axis of a stent.

Referring to FIG. 22A, an alternative embodiment of a stent 410 is shown flat layout. The stent 410 is formed of elongated strands 412 such as elastic metal wires. The wires 412 are woven to form a pattern of geometric cells 414. The sides 416a, 416b, 416c, and 416d of each of the cells 414 are defined by a series of strand lengths 418a, 418b, 418c, and 418d. Each of the sides 416 are joined to the adjoining side at an intersection where the strands 412 in this embodiment are either helically wrapped about each other to form interlocking joints 420 or joined to form a box node 422. The interlocking joints 420 are discussed above with respect to FIGS. 2A and 2B.

Figure 22B:
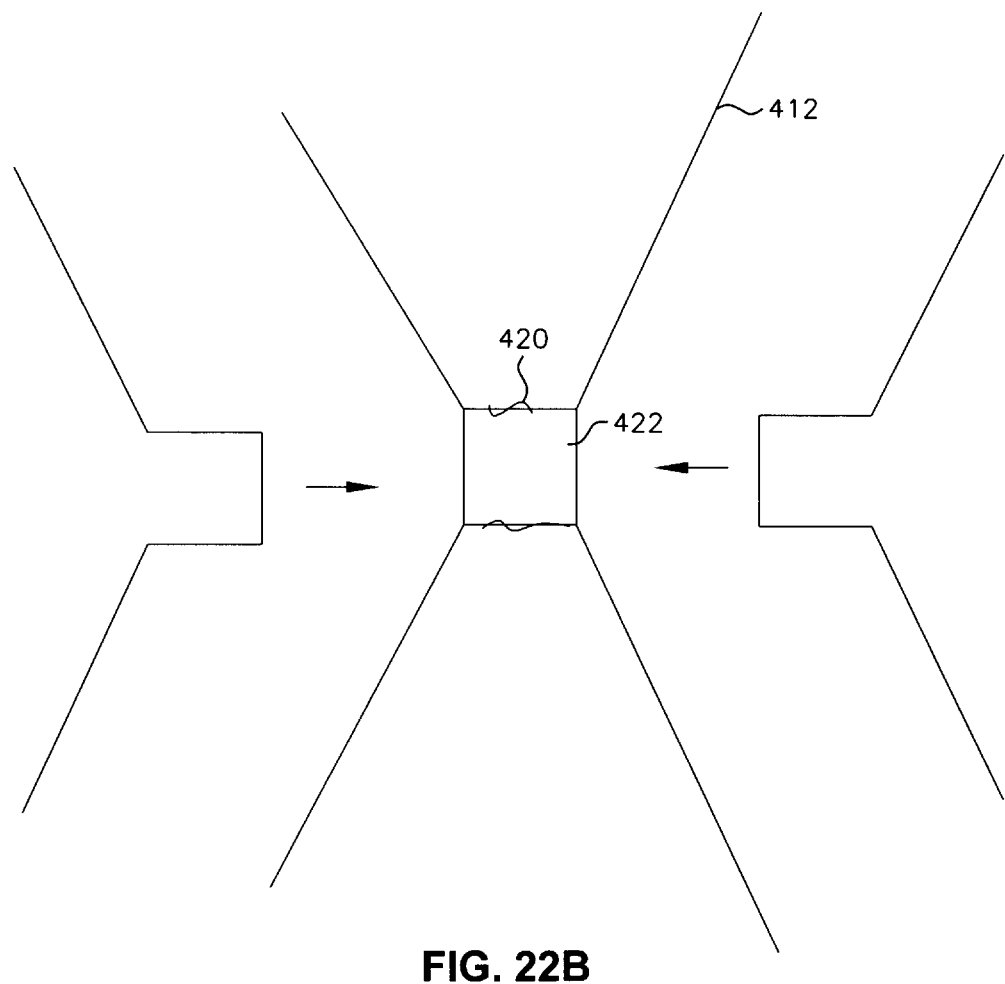
FIG. 22B is an enlarged portion of the stent taken at section 22B—22B in FIG. 22A.

Referring to FIG. 22B, the box node 422 is formed of a series of elements. The top of the box node 422 has an interlocking joint 420 where the strands 412 which extend from above cross each other. The strands 412 then extend down to form the sides of the box node 422. The strands 412 then cross each other on the bottom of the box node 422 in another interlocking joint 420. The respective strands therefore enter and exits the box node 422 from the same side. This is in contrast to the typical interlocking joint 420 or a cross joint, wherein the strands enter and exit at opposite corners of the joint. A cross joint is further explained above with respect to FIGS. 2A, 2B, and 3. The strands 412 are shown representing their path in exploded perspective view. (The interlocking joint 420 does not allow the strands 412 to normally separate like this.)

The box node constrains the displacement of the cell and introduces local stiffness. By varying the number of nodes and location of nodes the degree of stiffness can be controlled. With this approach, as required, the stent can have different local mechanical properties (radial strength, column strength, etc.) without compromising flexibility. For example, the ends of the stent can be significantly stiffer than the middle portion or vice versa. The node structure restricts dilation and foreshortening of the stent during flexing, bending, and extension.

Figure 23A:
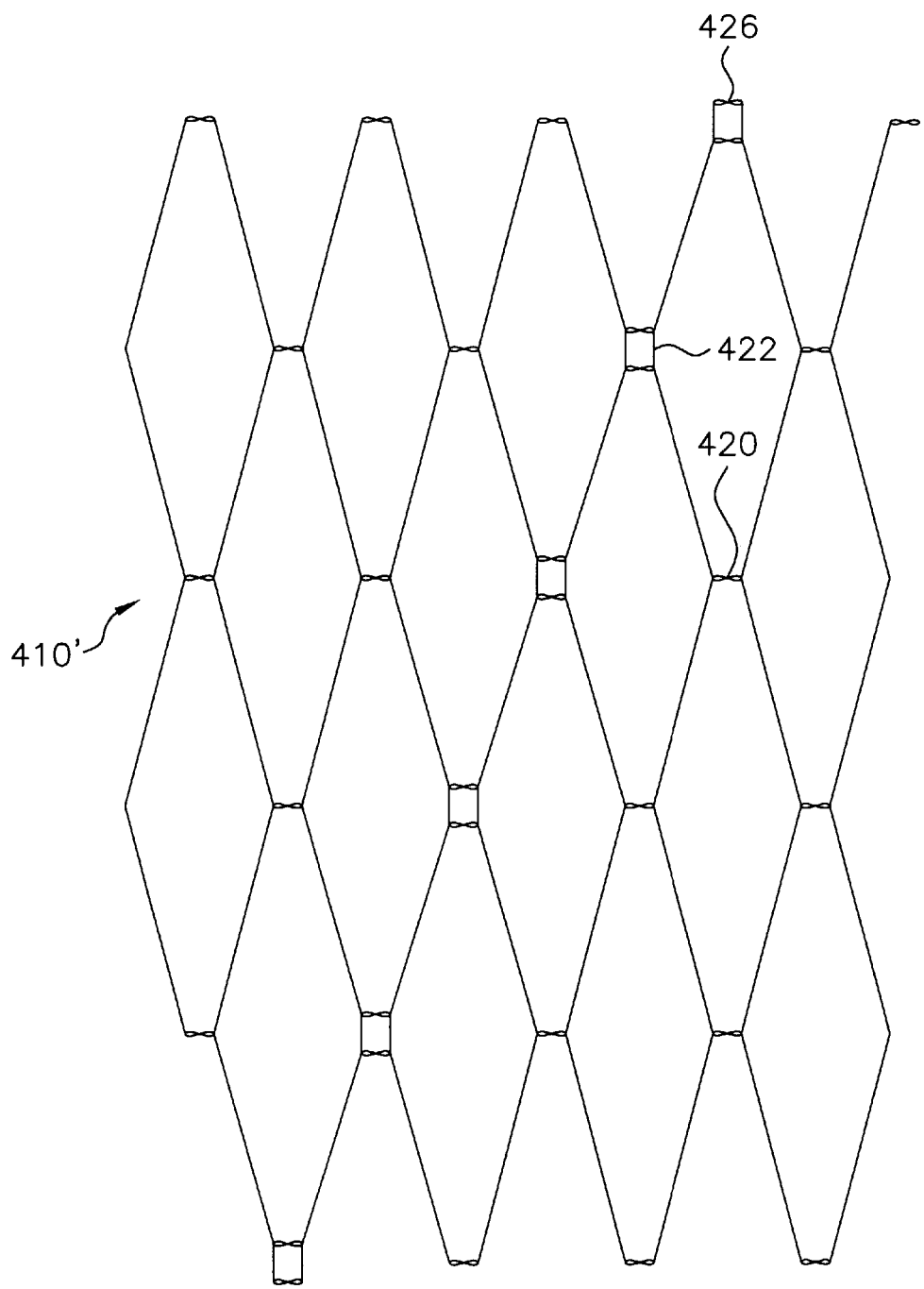
FIG. 23A is a flat layout view of another embodiment of the stent according to the invention.

FIG. 23A is a flat layout view of another embodiment of the stent 410'. In this embodiment, the stent 410' has a plurality of joints at the same level around the circumference of the tubular stents. The majority of the joints are interlocking joints 420. In this embodiment, one of the joints of the plurality of the joints around the circumference is a box node joint 422. The placement of the node joints 422 are located along a diagonal 426 of the stent 410.

Figure 23B:
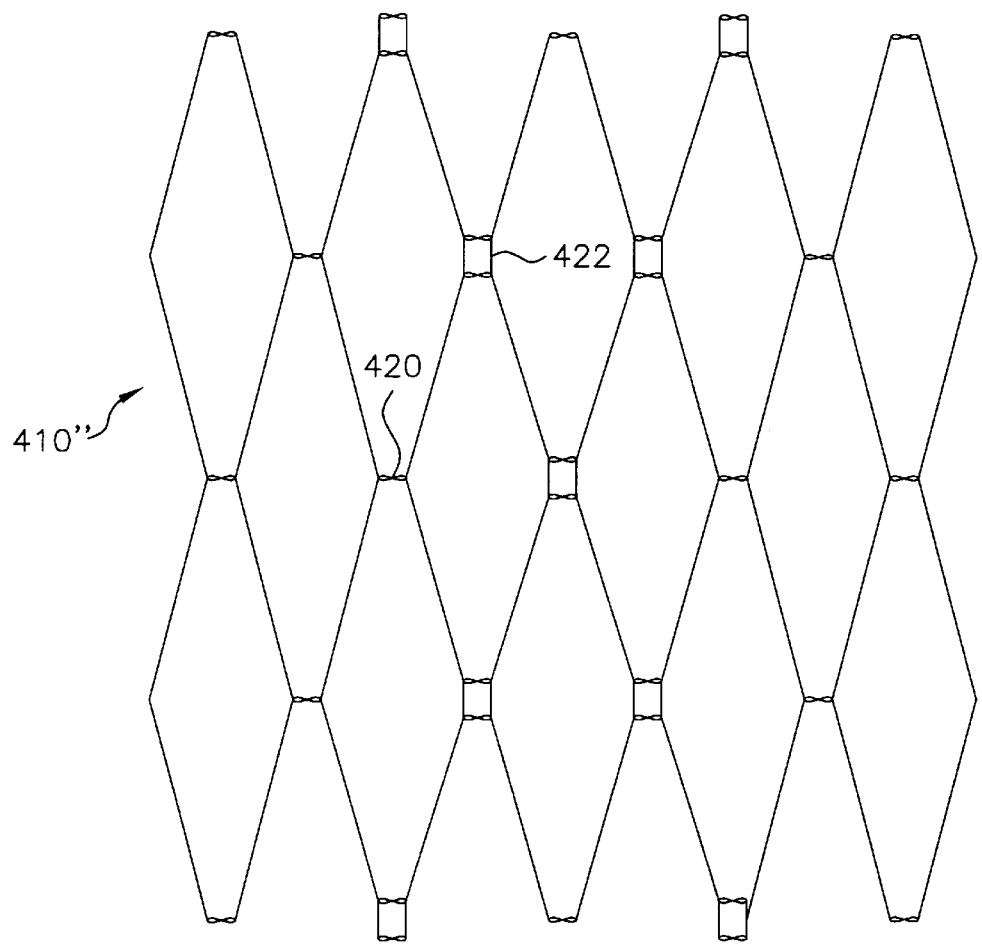
FIG. 23B is a flat layout view of another embodiment of the stent according to the invention.

FIG. 23B is a flat layout view of an alternative embodiment of the stent 410". In this embodiment, generally two joints of the plurality of the joints around the circumference is a box node joint 422. The placement of the box node joints are each along a diagonal. The diagonals are at any angle to each other, therefore in certain locations the box node joint for each diagonal is one in the same.

FIG. 24A is a schematic of an oblique view of a stent. The strands have been removed from FIG. 24B for clarity. The position of the box nodes are shown. In a preferred embodiment, the nodes are on alternating oblique planes. The nodes are located on opposing oblique planes. Positioning of the oblique planes also constitutes a pattern. The nodes may be placed on both oblique planes, as illustrated in FIG. 24B, also with a repeating pattern.

During deformation (bending, twisting, etc.) the oblique planes accommodate (dissipates) the transfer of forces and displacements instead of simply transmitting the deformation to the next region of the stent. Selecting the planes at opposing angles causes the stent to have a neutral response. Alternatively, the angle can be chosen to yield a preferred bending direction or plane. Locating the nodes on an oblique plane will cause the nodes to collapse in a staggered manner. When the stent is in a loaded conformation, the nodes will not co-locate in the same perpendicular plane. This increases the packing efficiency when in its loaded conformation.

Figure 25A:
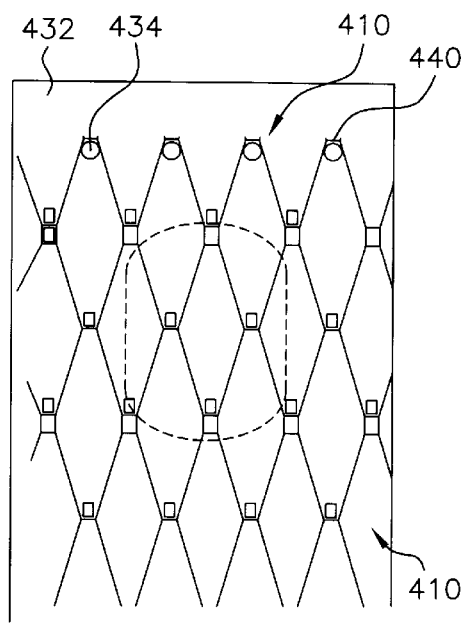
FIGS. 25A and 25B illustrate a mandrel for making a stent of FIGS. 22A–23B.
Figure 25B:
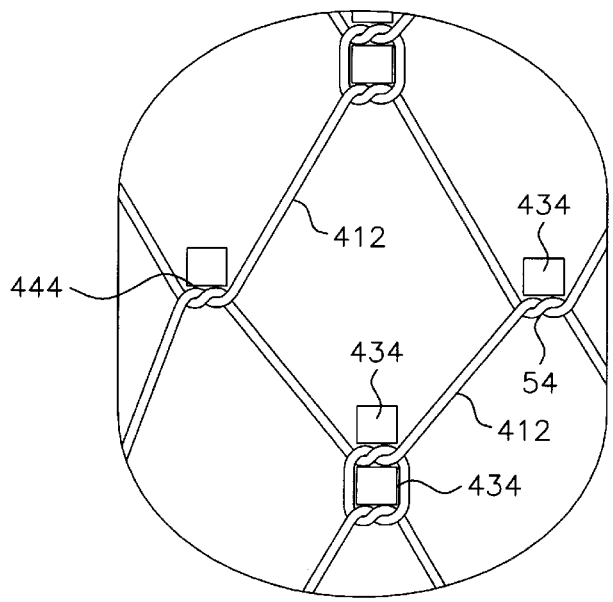

A method of making the stent 410 is shown in FIGS. 25A and 25B. A mandrel 432 has a plurality of pins 434 on the outer surface of the mandrel in a pattern that determines the geometric cell 436 pattern. The strands 412 are bent around the top portion 438 of each top anchoring pin 434 to form the proximal end 440 of the stent 410. The strands 412 are then pulled diagonally downward to an adjacent anchoring pin 434 where the strands 412 are joined. The strands 412 are helically wrapped about each other to form the interlocking joint 420, with each strand passing through a single 360 degree rotation. The two strands are pulled taught so that the interlocking joint 420 rests firmly against the bottom portion 444 of the anchoring pin 434 such that each strand 412 is maintained in tension.

Where a box node 422 is desired, the mandrel 432 has a pair of anchoring pins 434 for each box node 422. The strands 412 are helically wrapped about each other to form an interlocking joint 420 and positioned between the anchoring pins 434. The strands 412 extend down the sides of the lower anchoring pin 434. The strands 412 are then helically wrapped about each other to form the interlocking joint 420, with each strand passing through a single 360 degree rotation. The two strands are pulled taught so that the interlocking joint 420 rests firmly against the bottom portion 444 of the anchoring pin 434 such that each strand 412 is maintained in tension.

In a preferred embodiment, the anchoring pins 434 are square with the edges having appropriate radii. The square pins retain the helically wrap of the strands in a proper position.

The free ends of the strands 412 are then pulled downward to the next diagonally adjacent anchoring pin 434. This process is continued until the desired length of the stent 410 is achieved. The stent 410 is then heat-treated. The strands 412 at the joining end of the stent 410 are attached, for example, by ball welding or laser welding the ends of the wires as discussed above.

Figure 26A:
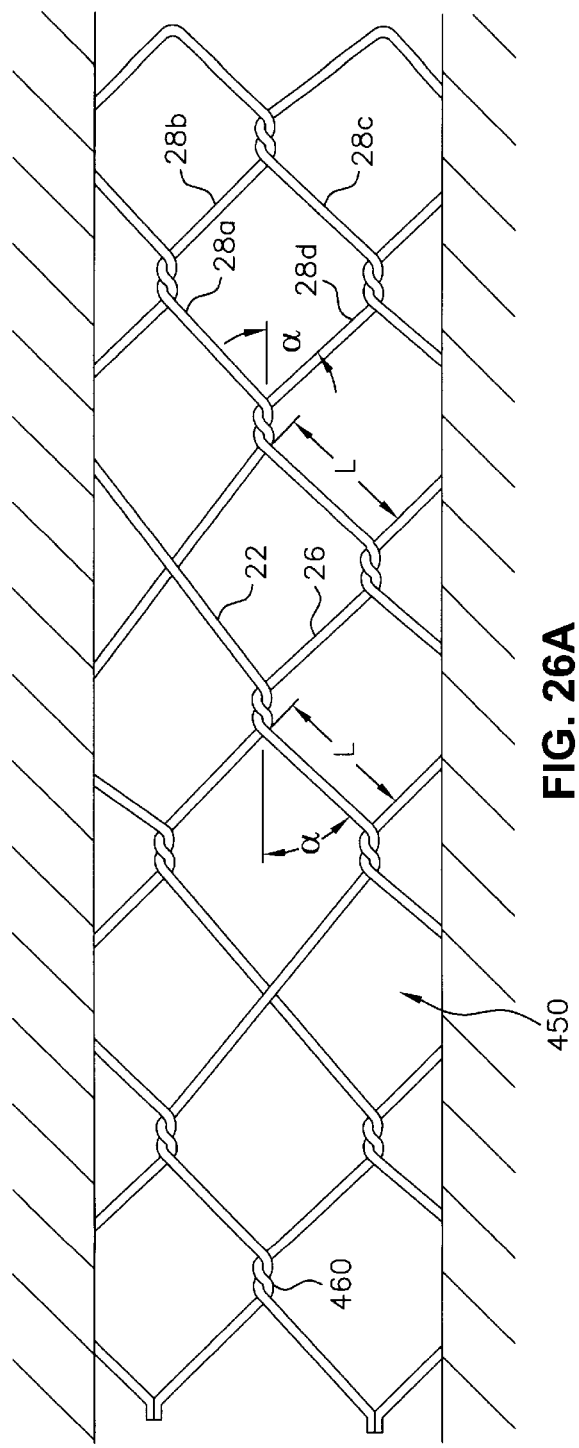
FIG. 26A is an enlarged cross-sectional view of a delivery tube containing an alternative embodiment of a low profile diamond metal stent.

An alternative stent 450 is shown in a contracted position within the sleeve 452 in FIG. 26A. Similar to previous embodiment, the stent 450 is formed of elongated strands 22 such as elastic metal wires. The wires 22 are woven to form a pattern of geometric cells 24. The sides 26a, 26b, 26c, and 26d of each of the cells 24 are defined by a series of strand lengths 28a, 28b, 28c, and 28d. Each of the sides 26 are joined to the adjoining side at an intersection where the strands 22 are helically wrapped about each other to form interlocking joints 460. In contrast to the previous embodiments, the helically wrapped joints 460 extend longitudinal in contrast to radial. A medical prosthetic stent with longitudinal joints and method of manufacturing such a stent is described in U.S. Pat. No. 5,800,519 on Sep. 1, 1998 and which is incorporated herewith by reference.

The strand angle α is increased in the compressed or constrained state of the stent in this embodiment. The strand angle can be in the range of 10°–80° depending upon the particular embodiment. Smaller strand angles between 10° and 45° often require a shortened cell side length L to maintain radial expansion force. Cell side lengths L in the range of 0.5 to 4 mm, for example, can be used with stent having these smaller strand angles. For stents with larger strand angles in the range of 3–8 mm can be used, depending on the expanded diameter of the stent, the number of cells and the desired radial expansion force.

Figure 26B:
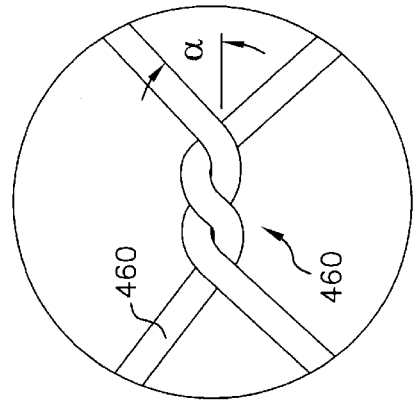
FIG. 26B is an enlarged portion of the stent taken at section 26B—26B in FIG. 26A.

In addition to FIGS. 26A and 26B where the joints extend longitudinal, it is recognized that other embodiments such as the box node can extend longitudinal.

Figure 27A:
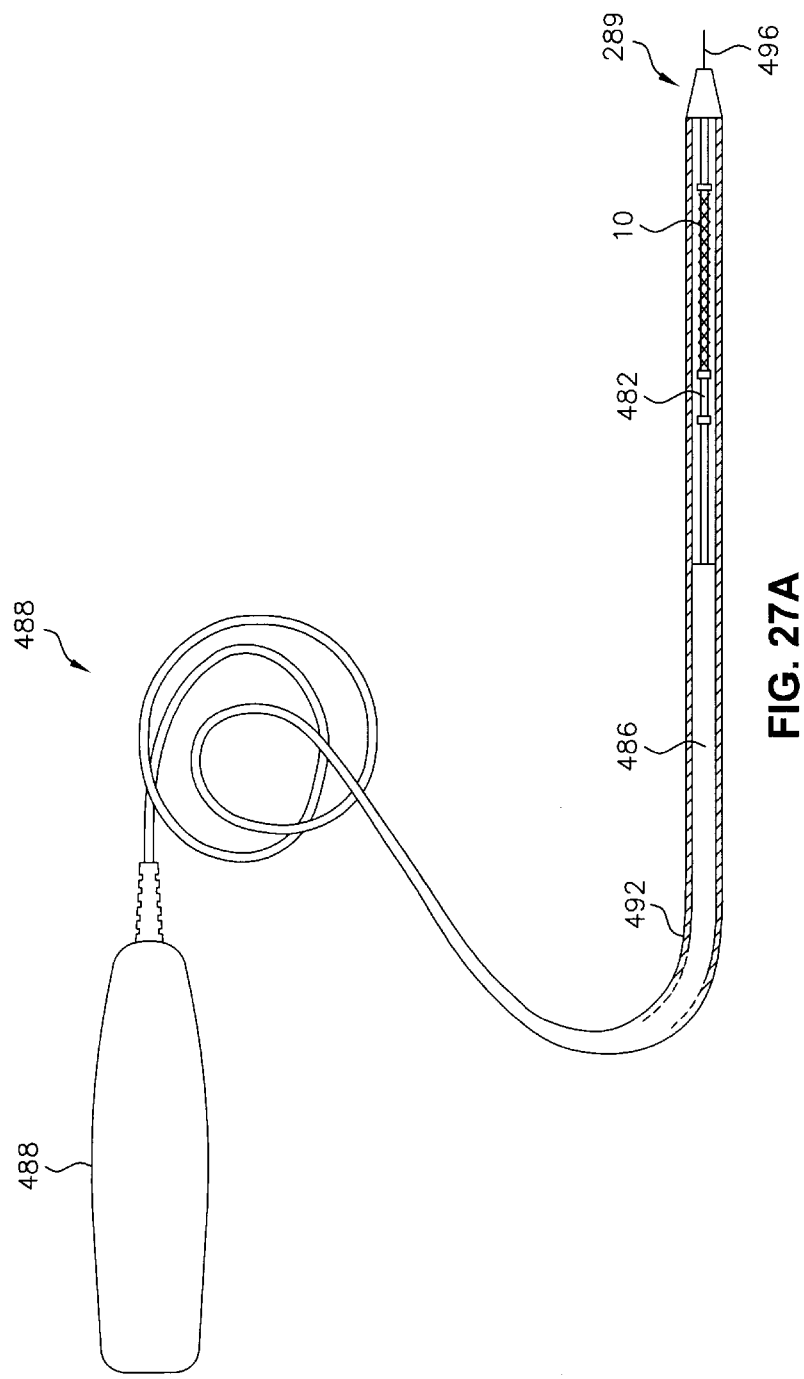
FIG. 27A is a side view of a coaxial delivery system with portions broken away.

Several delivery systems have been discussed above. It is recognized that an alternative delivery system 480, that of a coaxial delivery system 480, can be used. Referring to FIG. 27A, a stent 10 is positioned over an inner shaft 482, which is a braided tube in a preferred embodiment at a distal end of the delivery system. The inner shaft 482 extends from a handle 484 located at the proximal end. The delivery system has an outer shaft 486 which extends from the proximal handle 484 to a point, which is proximal to the distal end 488. The inner shaft 482 extends through a lumen 490 of the outer shaft from the proximal handle 484 and projects out the distal end of the outer shaft. The inner shaft 482 is free-floating within the lumen of the outer shaft 486.

An outer sheath 492 overlies the inner shaft 482 and the outer shaft 486 from the distal end 488 to the proximal handle 484. This is in contrast to previous delivery systems discussed wherein the outer sheath 492 ends at a point distal to the handle. The outer sheath 492 is movable relative to the inner shaft 482 and the outer shaft 486 by pulling the outer sheath 492 at the proximal handle end. A guide wire 496 extends through the inner shaft from the proximal handle to the distal end.

Figure 27B:
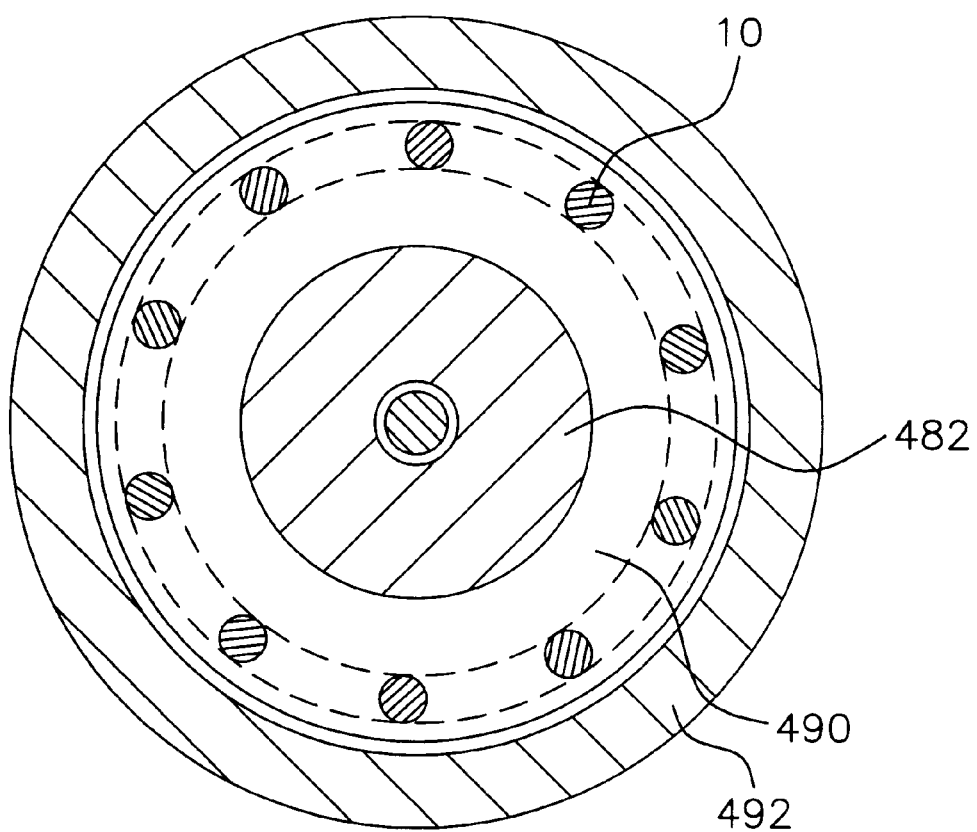
FIG. 27B is a sectional view taken along line 27A—27A of FIG. 27A.

Referring to FIG. 27B, a sectional view of the inner shaft 482 projecting from the lumen 490 of the outer shaft 486 is shown. The outer sheath 492 is coaxial with the inner shaft 482 and the outer shaft 486. The properties of the inner shaft 482, outer shaft 486, and outer sheath 492 can be similar to those discussed above with respect to other embodiments.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A stent delivery system comprising:
   a catheter having an inner shaft with a distal end and a proximal end;
   an outer shaft disposed around the inner shaft, wherein the outer shaft is movable relatively to the inner shaft;
   a handle attached to the proximal end of the catheter;
   a stent concentrically arranged around a distal region of the inner shaft, wherein a guide wire is disposed in a lumen of the inner shaft; and
   a sheath extending around the inner shaft and the stent, the sheath having a composite structure and being coupled to an actuator on the handle with a wire such that the sheath can be moved longitudinally relative to the inner shaft in response to the movement of the actuator.

2. The stent delivery system of claim 1 wherein the sheath has a proximal end and a distal end and a material property of the sheath varies from the proximal end to the distal end of the sheath.

3. The stent delivery system of claim 1 wherein the composite structure comprises a braid or coil structure.

4. The stent delivery system of claim 1 further comprising a coupling element connected to the outer sheath and extending within the catheter from the outer sheath to the proximal end.

5. The stent delivery system of claim 1 wherein the inner shaft has a plurality of concentric layers including a tubular support layer and a covering layer over the support layer.

6. A stent delivery system comprising:
   a catheter having an inner shaft with a distal end and a proximal end, wherein a guidewire is disposed within a lumen of the inner shaft;
   a handle attached to the proximal end of the catheter;
   an outer shaft disposed around the inner shaft, wherein the outer shaft is movable relatively to the inner shaft;

a stent mounting platform extending concentrically around a distal section of the inner shaft, wherein a guide wire is disposed in a lumen of the inner shaft;

a sheath with a proximal end and a distal end, the sheath having a plurality of layers such that a material property of at least one of the layers of the sheath varies from the proximal end to the distal end of the sheath; and an actuator on the handle, the actuator being coupled to the sheath with a wire such that the sheath can be moved relative to the stent mounting platform with the actuator.

7. The stent delivery system of claim 6 wherein the plurality of layers of the sheath include an inner layer of a fluorinated polymer, a second layer encircling the inner layer and comprising a polyurethane, a third layer encircling the second layer, and a fourth layer having a varying property material including a relative high durometer material and a relative low durometer material.

8. The stent delivery system of claim 7 wherein the third layer is a polymer.

9. The stent delivery system of claim 7 wherein the third layer is a metal braid.

10. The stent delivery system of claim 6 wherein the sheath comprises a coiled or a braided structure.

11. The stent delivery system of claim 6 wherein the material property comprises stiffness of the sheath, the sheath having a first stiffness along a proximal section and a lower stiffness along a distal section.

12. The stent delivery system of claim 6 wherein the first layer comprises a first material and the second layer comprises a second material different from the first material.

* * * * *